(12) United States Patent
Peabody et al.

(10) Patent No.: US 9,943,580 B2
(45) Date of Patent: Apr. 17, 2018

(54) MALARIA VACCINE

(71) Applicants: STC.UNM, Albuquerque, NM (US); LEIDOS, INC, Reston, VA (US)

(72) Inventors: David S. Peabody, Albuquerque, NM (US); Bryce Chackerian, Albuquerque, NM (US); James Pannucci, Frederick, MD (US); Gabriel M. Gutierrez, Kensington, MD (US); Amy Rene Noe, San Diego, CA (US); Scott Budd Winram, Frederick, MD (US); Steve Chienwen Huang, Germantown, MD (US)

(73) Assignees: STC.UNM, Albuquerque, NM (US); LEIDOS, INC., Reston, VA (US)

( * ) Notice: Subject to any disclaimer, the term of this patent is extended or adjusted under 35 U.S.C. 154(b) by 0 days.

(21) Appl. No.: 15/023,653

(22) PCT Filed: Sep. 11, 2014

(86) PCT No.: PCT/US2014/055087
§ 371 (c)(1),
(2) Date: Mar. 21, 2016

(87) PCT Pub. No.: WO2015/038708
PCT Pub. Date: Mar. 19, 2015

(65) Prior Publication Data
US 2016/0228525 A1    Aug. 11, 2016

Related U.S. Application Data

(60) Provisional application No. 61/877,039, filed on Sep. 12, 2013.

(51) Int. Cl.
| | |
|---|---|
| *A61K 39/39* | (2006.01) |
| *A61K 39/015* | (2006.01) |
| *C12N 7/00* | (2006.01) |
| *C12N 15/10* | (2006.01) |
| *A61K 39/00* | (2006.01) |
| *A61K 35/76* | (2015.01) |

(52) U.S. Cl.
CPC ............ *A61K 39/015* (2013.01); *A61K 39/39* (2013.01); *C12N 7/00* (2013.01); *C12N 15/1037* (2013.01); *A61K 35/76* (2013.01); *A61K 2039/5256* (2013.01); *A61K 2039/5258* (2013.01); *A61K 2039/55566* (2013.01); *C07K 2319/40* (2013.01); *C12N 2795/18122* (2013.01); *C12N 2795/18123* (2013.01); *C12N 2795/18134* (2013.01)

(58) Field of Classification Search
None
See application file for complete search history.

(56) References Cited

FOREIGN PATENT DOCUMENTS

| | | |
|---|---|---|
| WO | 2011082381 A2 | 7/2011 |
| WO | 2013003353 A2 | 1/2013 |
| WO | 2013063366 A2 | 5/2013 |
| WO | 2013106525 A1 | 7/2013 |

OTHER PUBLICATIONS

Oliveira et al. (Infect. Immun., 73:3587-3597, 2005).*
Rodriguez D, et al. Vaccine Efficacy Against Malaria by the Combination of Porcine Parvovirus Like Particles and Vaccinia Virus Vectors Expressing CS of Plasmodium. Plos One, 2012;7(4):1-10. See abstract.
Vijayan A, et al. Adjuvant Like Effect of Vaccinia Virus 14K Protein: A Case Study with Malaria Vaccine Based on the Circumsporozoite Protein. J Immunol, 2012;188(12):6407-6417.
Cohen et al., Nature 192:733-737, 1961.
Sabchareon et al.; Am J Trop Med Hyg, 45(3):297-308, 1991.
Douglas et al., Nat Commun, 2:601, 2011.
Baum et al., Int J Parasitol, 39(3):371-380, 2009.
Chen et al., PLoS Pathog, 7(9):e1002199, 2011.
Williams et al., PLoS Pathog, 8(11):e1002991, 2012.
Patel et al., J Infect Dis, 208(10):1679-1687, Nov. 15, 2013.
Caldeira et al., Vaccine, 28(27):4384-4393, 2010.
Peabody, Arch Biochem Biophys, 347(1):85-92, 1997.
Peabody et al., Nucleic Acids Res, 24(12):2352-2359, 1996.
Peabody et al., J Mol Biol, 380(1):252-263, 2008.
Chackerian et al., J Mol Biol, 409(2):225-237, 2011.
Ord et al., PLos One, 7(1):e30251, 2012.
Oliveira et al., Infection and Immunity, 73(6):3587-3597, 2005.

* cited by examiner

*Primary Examiner* — Brian Gangle
(74) *Attorney, Agent, or Firm* — Henry D. Coleman; R. Neil Sudol

(57) ABSTRACT

Embodiments are directed to malaria vaccines comprising a bacteriophage VLP displaying a heterologous peptide identified by affinity selection as an anti-malaria mimotope.

14 Claims, 15 Drawing Sheets

SAI1068: rRH5 expressed in wheat germ system.
SAI1468: rRH5 expressed in E. coli.
SAI166: rRH5 expressed in pseudomonas.

MFENAIKKTKNQENNLTLLPIKSTEEEKDDIKNGKDIKKEIDNDKENIKTNNAKDHSTY
IKSYLNTNVNDGLKYLFIPSHNSFIKKYSVFNQINDGMLLNEKNDVKNNEDYKNVDYK
NVNFLQYHFKELSNYNIANSIDILQEKEGHLDFVIIPHYTFLDYYKHLSYNSIYHKSSTYG
KCIAVDAFIKKINETYDKVKSKCNDIKNDLIATIKKLEHPYDINNKNDDSYRYDISEEIDD
KSEETDDETEEVEDSIQDTDSNHTPSNKKKNDLMNRTFKKMMDEYNTKKKKLIKCIK
NHENDFNKICMDMKNYGTNLFEQLSCYNNNFCNTNGIRYHYDEYIHKLILSVKSKNL
NKDLSDMTNILQQSELLLTNLNKKMGSYIYIDTIKFIHKEMKHIFNRIEYHTKIINDKTKII
QDKIKLNIWRTFQKDELLKRILDMSNEYSLFITSDHLRQMLYNTFYSKEKHLNNIFHHLI
YVLQMKFNDVPIKMEYFQTYKKNKPLTQ

FIG. 6

```
8_LSGGWPE ------- L-SGGWPE --- 7
12_LSGGWPEG ------ L-SGGWPEG -- 8
186_LLDSGQW ------ LLDSGQW ----- 7
64_LRDANP ------- L--RDANP --- 6
155_GQKLGDI*QE ---- GQKL--GDIQE --- 9
14_WTTGGPTH ---- WTTGGPTH ------ 8
55_RWPTGAPC --- RWPTGAPC -------- 8
113_WLAGLKE ---- WLAGLKE ------- 7
137_WLAGLKEG ---- WLAGLKEG ------ 8
192_AGLTNGVPGT ------ AGLTNGVPGT -- 10
19_GTGLGN ------ GTG-LGN ------ 6
150_SPADTGLGAR --SPADTG-LGAR------ 10
34_HWTGHGAY ---- HWTG-HGAY ----- 8
72_AGKGAHN ---- AGKGAHN ------- 7
75_AGKGAHNG ---- AGKGAHNG ------ 8
81_WDGG*HN*AI ----- WDGGHNAI ----- 8
29_WCLGGSS ------ WCLGGSS ---- 7
200_AAGWGGSD ---- AAGW--GGSD ---- 8
105_ARLAGWME ------- ARLAGWME ---- 8
133_GGSGVME ------ GG-SGVME ---- 7
47_DTGG*VG ---- DTGGV--G ------ 6
171_GGVDTGWH ------- GGVDTGWH ---- 8
68_ASGVNRGG ---- ASGVNRGG ------ 8
86_EGVWRAGD ----- EGVWRAGD ----- 8
108_SAGGLDRGTI ---- SAGGLDRGTI ---- 10
124_GVSDRGQ ------- GVSDRGQ ----- 7
45_AGPMPVTAAS ------ AGPMPVTAAS --- 10
146_SYPAGP ------- SYP--AGP --- 6
143_GSSGPVQVTG ----- GSSGPVQVTG --- 10
183_PATVVG -------- PATVVG --- 6
76_PRGDMG -------- PRGDMG --- 6
178_QICFMPDGSA ---- QICFMPDGSA ---- 10
10_CWAGHVRGQQ CWAGHVRGQ--Q ----- 10
161_RGSQIQ ------ RGS--QIQ ---- 6
195_VRGLIP ----- VRG---LIP ---- 6
30_TTQEGK -------- TT--QEGK --- 6
125_VRGTQMGS ----- VRGT--QMGS ---- 8
131_QRGGGALVPR ----- QRGGGALVPR --- 10
162_RGGRWEG ------ RGG-RWEG ---- 7
49_AARGEEAA ---- AARGE---EAA --- 8
112_CGTEGLV ------ CGTEGLV ------- 7
181_TPGLGLQLAR ----- TPGLGLQLAR --- 10
3_ESGCDGRK ---ESGCDGRK-------- 8
92_SG*STGRN ---- SGSTGRN ------- 7
31_EAKGRL ------ EAKGRL -------- 6
50_GGYGASGR ------ GGYGASGR -------- 8
```

FIG. 12A

```
46_GRPGCN ------GRPGCN------- 6
173_RRGRPGE ----RRGRPG-E-------- 7
39_GRAGMKST -----GRAGMKST------ 8
111_SGGMAGRGM ---SGGMAGRGM------- 9
115_SGGMAGRGMG ---SGGMAGRGMG------ 10
79_GGQAGHRR -----GGQAGHRR-------- 8
89_RAEGGGRQ ---RAEGG-GRQ-------- 8
157_SRCKGGQGQT -SRCKGGQGQT-------- 10
84_RFDGRGRS ---RFDGR-GRS-------- 8
154_IPGGRYQR ---IPGG--RYQR------- 8
190_GPGRRC ----GPGR--RC------- 6
70_GRAVCA ------GRAVCA-------- 6
117_GRTVSA ------GRTVSA-------- 6
158_GRSVEHHRSD -------GRSVEHHRSD--- 10
20_NRTTGRSS ------NRTTGRS-S----- 8
40_ANGRER -----ANGRER--------- 6
41_ANGRERGD -----ANGRERGD------- 8
164_MLNNRCRD ----MLNNRCR-D------ 8
142_GTADACRQHC ---GTADACRQHC----- 10
168_LANAGRSH -----LANAGRSH------- 8
23_VGASRRRR -----VGASRRRR------- 8
91_VGWSRRRR -----VGWSRRRR------- 8
53_PGETVGSSRS PGETVGSSRS--------- 10
189_GTVHQRRS -G-TVHQRRS--------- 8
77_YVG*EYI ---YVGE-YI--------- 6
191_FYHGDSHS --FYHGDSHS--------- 8
25_RVRCGSSA -RVRCGSSA----------- 8
152_PLRVGSS -PLRVGSS----------- 7
83_RSRRGSET -RSRRGSET---------- 8
85_GQSRTPSDTC GQSRTPSDTC--------- 10
6_WAPFQH ------WAPFQH------ 6
119_WKSGQH -------WKSGQH------ 6
123_LKTRQVWK -LKTRQVWK---------- 8
126_LKTRQVWKGD -LKTRQVWKGD-------- 10
122_RIVWAWKE ---RIVWAWKE--------- 8
78_CVKDYESASF ---CVKDYESASF----- 10
153_KSYGRARY -----KSYGRARY------ 8
99_KSCQKERH -----KSCQKERH------- 8
9_RSAQGH ------RSAQGH------- 6
144_HMKAQYHS -----HMKAQYHS------- 8
65_NFRYCSLARS ---NFRYCSLARS------ 10
95_GAPWARSG ------GAPWARSG---- 8
54_HMRSSSMVLL ---HMRSSSMVLL------ 10
196_RARRMVA ------RARRMVA------ 7
87_ARPSVLH ------ARPSVLH------ 7
169_HSEEYPSMLL ----HSEEYPSMLL----- 10
```

FIG. 12B

32_CVVYFRLNSN ---CVVYFRLNSN--- 10
106_YYGTLSNS ------YYGTLSNS--- 8
7_GAVHASER ------GAVHASER----- 8
138_TAKRASDRNT ------TAKRASDRNT--- 10
16_KKRSFD* ------KKR-SFD--- 6
43_HKKESRS ------HKKE-SRS---- 7
26_TRSEDSVT ------TRSEDSVT---- 8
28_APDKNSRVTQ -----APDKNSRVTQ--- 10
18_GVPKSH -----GVPKS--H----- 6
159_CMTGNDKSDR --CMTGNDKS--DR---- 10
129_GNDKDRVDRR ------GNDKDRVDRR--- 10
132_ISTFGTT ---ISTFGTT-------- 7
141_ISTFGTTGEL ---ISTFGTT--GEL--- 10
35_FTFTTTGY ----FTFTTT--GY---- 8
38_FDKTKW ------FDKT--KW---- 6
52_SFQLRK ---SF-QLRK-------- 6
177_S*VRQK*RKV ---SVRQKRKV-------- 8
120_VAADRKVGT ----VAADRKVGT------ 9
121_VAADRKVGTG ----VAADRKVGTG---- 10
1_VCLRRF -------VC---LRRF-- 6
69_REVCVPR -----REVC---VPR---- 7
2_LTQVNYV -----LTQ---VNYV--- 7
74_KCLRQP ------KC---LRQP--- 6
17_QALSNF ---QALSN---F------ 6
160_ALDNTTYEQS -----ALDNTT-YEQS--- 10
148_LVNITRL ------LVN---ITRL---- 7
57_LCRLKPRLRN --LCRLKPR---LRN---- 10
127_LKPLTP ------LKP---LTP---- 6
97_IKSPLASRPF ---IK-SP---LASRPF 10
188_KCSPLIN -----KCSP---LIN---- 7
71_GANASPLR --GANASP---LR------ 8
51_VAVRPSAA ------VAVR-PSAA---- 8
82_GLGVEVQPDA ---GLGVEVQ-PDA--- 10
185_LVAVIFST -----L-VAVI-FST---- 8
62_QVVPVMRT ----QVVPVM-RT------ 8
p165_FVIPVRC ----FVIPV--RC----- 7
5_PTVHCSA ------PTVH-CSA---- 7
98_ALPTYHLS -----ALPTYH-LS------ 8
107_VKAGACSAIS -----VKAGA-CSAIS-- 10
145_CNRACPAI ----CNR-A-CPAI--- 8
44_GAYTSK --------GAY-TSK---- 6
197_NMPQAYAS ----NMPQAY-AS----- 8
116_PGAVTGYA ------PGAV-TGYA--- 8
134_GAWTRVA -------GAW-TRVA--- 7
90_PGTMAPAA ------PGTM-APAA--- 8

FIG. 12C

149_EGAKAMAA ------EGAK-AMAA--- 8
63_QPAMGA --------QP-AMGA--- 6
56_LVPSRWT -----LVPSRW-T------ 7
59_LVPSRWTG -----LVPSRW-TG----- 8
163_NVPAAWNQYN ----NVPAAW-NQYN--- 10
27_CESVPGAG --------CE-SVPGAG- 8
136_CESVPG --------CE-SVPG--- 6
180_VQEACESDPH -----VQEACE-SDPH--- 10
61_RTVRECEQ ------RTVR-ECEQ--- 8
110_VRAGEARR ------VRAG-EARR--- 8
140_RAEMPY ------RAEM-PY----- 6
174_RAEHVRVAER ------RAEH-VRVAER- 10
104_RACGPCK ------RACG-PCK---- 7
11_GFHSPMSQRN ----GFHSPM-SQRN--- 10
151_SAHQPRCQ ----SAHQPR-CQ----- 8
37_RHDVSCGF ------RHDVS-CGF---- 8
194_VRHDVVDQMI ----VRHDVV-DQMI--- 10
94_KQGRHLQAGT -----KQGRH-LQAGT-- 10
128_HQGPRLI ------HQGPR-LI----- 7
170_GVCSDKWK -------GVC-SDKWK-- 8
182_QGVLVD ------QGVL-VD----- 6
184_NQQGMRSD ----NQQGMR-SD----- 8
4_CGTAVA ------CGT---AVA---- 6
36_CNTSVS ------CNT---SVS---- 6
88_WNTHTLLWGT ------WNT---HTLLWGT 10
96_TR*ALP ------TRA---LP----- 5
114_TR*ALPGA -----TRA---LPGA--- 7
139_RPLVCRALPS -RPLVCRA---LPS---- 10
101_SRDLPRDS ------SRD---LPRDS-- 8
135_DCRTLA ----DCRT---LA------ 6
175_ETEFFMSRKL ------ETEFFMSRKL-- 10
179_ETLTFK ------ET---LTFK--- 6
24_VEPNPFL ------VEP---NPFL--- 7
58_NDFLASTT --NDFLAS---TT------ 8
172_STSTTFP ------STS---TTFP--- 7
80_WHSSEFRGKY ------WHS---SEFRGKY 10
109_HTEVFRD ------HT---EVFRD-- 7
93_LVL*YLAFRR ----LVLY---LAFRR-- 9
199_AFRFENDP ------AFR---FENDP-- 8
33_VLGSNS --------V---LGSNS-- 6
166_SQDIRAVLGS -SQDIRAV---LGS---- 10
67_VLGKTCD --------V---LGKTCD- 7
103_*MH*ARLRVE ------MHAR---LRVE--- 8
118_ACAVLR ----ACAV---LR----- 6
42_SAIKKPVT ----SAIKKPVT------ 8
130_TAIKKMKS -----TAIKKMKS------ 8

FIG. 12D

13_VAIKRPGKGT -----VAIKRPGKGT--- 10
60_LASLGAGKCK -----LASLGAGKCK--- 10
156_VAILGADY -----VAILGADY---- 8
15_WRTEII -------WRTEII----- 6
198_GEGWRDER ----GEGWRDER------ 8
102_KGAGWRW ----KGAGWRW-------- 7
187_KGAGWRWG ----KGAGWRWG------- 8
66_EYRQSRR -------EYRQSRR----- 7
100_INMRQSKS -----INMRQSKS----- 8
167_LEMRKN -----LEMRKN------- 6
48_RKSASQKGMC -----RKSASQKGMC--- 10
22_MVEQSGEVSN ----MVEQSGEVSN---- 10
21_RN*SGYF -----RNSGYF------- 6
73_STHDHEVL -----STHDHEVL----- 8
147_RPEQSRDGAT ----RPEQSRDGAT---- 10
176_CQLTAFP -----CQLTAFP------ 7
193_WQQVPFCSHH -----WQQVPFCSHH--- 10

FIG. 12E

MALARIA VACCINE

PRIORITY CLAIM

This application is a United States national phase patent application based upon international patent application no. PCT/US2014/055087 filed Sep. 11, 2014, which claims priority to U.S. Provisional Patent Application Ser. No. 61/877,039 filed Sep. 12, 2013, both of which applications are incorporated herein by references in their entirety herein.

STATEMENT REGARDING FEDERALLY FUNDED RESEARCH

This invention was made with government support under AI-N01-045210 awarded by NIAID/DMID. The government has certain rights in the invention.

BACKGROUND

I. Field of the Invention

Embodiments are directed generally to medicine, immunology, and microbiology. In particular embodiments are directed to malaria vaccines.

II. Description of Related Art

Malaria is a mosquito-borne infectious disease of humans and other animals caused by parasitic protozoans of the *Plasmodium* type. Most deaths are caused by *P. falciparum* with *P. vivax, P. ovale,* and *P. malariae* generally causing milder forms of malaria. Malaria causes symptoms that include fever, fatigue, vomiting, and headaches. In severe cases it can cause yellow skin, seizures, coma, or death. These symptoms usually begin ten to fifteen days after being bitten by a mosquito carrying *plasmodium*. For subjects who have recently survived an infection, re-infection typically causes milder symptoms.

Natural clinical immunity to malaria develops slowly, is only temporary in the absence of repeated natural infection, and is strain-specific. The immune correlates of protection are only partially understood, but have long been known to involve antibodies to blood stage forms of the parasite (Cohen et al., *Nature,* 192:733-737, 1961; Sabchareon et al., *Am J Trop Med Hyg,* 45(3):297-308, 1991). A number of proteins are implicated in *Plasmodium faliciparum*'s ability to target and enter erythrocytes. However, many of these proteins are highly polymorphic, making development of a vaccine effective across different strains of *P. falciparum* challenging. A recent study of ten different proteins present on malarial blood-stage parasites showed that the protein called reticulocyte-binding protein homolog 5 (or Rh5) was the most effective at eliciting neutralizing antibodies (Douglas et al., *Nat Commun,* 2:601, 2011). RH5 is one of the essential proteins involved in merozoite invasion of erythrocytes and has a lower level of polymorphism among strains compared to other malaria vaccine targets (Baum et al., *Int J Parasital,* 39(3):371-380, 2009; Chen et al., *PLoS Pathog,* 7(9):e1002199, 2011). Remarkably, a recent study indicated that sera from individuals in a holoendemic malaria region of Africa show very "minimal acquisition" of anti-Rh5 antibodies (Williams et al., *PLoS Pathog,* 8(11): e1002991, 2012). This suggests that despite its promise as a vaccine antigen, RH5 is not particularly immunogenic during natural malaria infection. Nevertheless, it has recently been shown that although they are not very abundant, anti-RH5 antibodies present in infected individuals can inhibit parasite invasion of red blood cells, in vitro (Patel et al., *J Infect Dis,* 2013). Taken together, these data reflect the opportunity for an RH5-based vaccine to provide effective cross strain protection in humans. Therefore, RH5 is being pursued as a good target for future vaccine development against *P. falciparum.*

There remains a need for additional compositions and methods for prevention and treatment of malaria.

SUMMARY

Embodiments are directed compositions and methods for treating or preventing malaria. Certain aspects are directed to a malaria vaccine. In a further aspect malaria vaccines comprise an MS2 VLP modified with an antigenic heterologous peptide identified by affinity selection of peptide mimotopes on the MS2 VLP platform. Embodiments include anti-malaria vaccines, immunogenic compositions comprising populations of VLPs, methods of raising an immunogenic response, and methods for reducing the likelihood of a subsequent malaria infection after immunization.

Certain embodiments are directed to a peptide comprising an anti-malaria epitope. In certain aspects the epitope comprises at least one epitope of the amino acid sequence AIKK (SEQ ID NO: 227) or AIKR (SEQ ID NO: 228). In certain aspects the peptide is 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more amino acids in length having one or more epitopes of $AIKX_{KR}$ where $X_{KR}$ is a K (lysine) or R (arginine) amino acid residue (SEQ ID NO: 226). In certain aspects the peptide has a consensus sequence of $(X)_n AIKX_{KR}(X)_m$ (e.g., SEQ ID NO:4), wherein n is an integer from 0 to 36 and m is an integer from 0 to 36, each X is independently any amino acid and $X_{KR}$ is a single K (lysine) or R (arginine) amino acid residue. In certain aspects the core amino acid sequence $AIKX_{KR}$ (SEQ ID NO: 226) starts at position 2, 3, 4, 5, 6, 7, 8, 9, 10, 11, 12, 13, 14, 15, 16, 17, 18, 19, or 20 of the peptide. In certain aspects the core amino acid sequence starts at position 1, 2, 3, 4, 5, or 6. In a further aspect the peptide is incorporate into a antigen delivery platform, e.g., liposome, virus-like particle, peptide-conjugate, and the like.

Certain embodiments are directed to compositions comprising an RNA bacteriphage virus like particle (VLP) displaying a heterologous Certain aspects include a therapeutic or immunogenic composition comprising one or more VLP displaying one or more peptides having an amino acid sequence selected from SEQ ID NO:2, 3, 206, 207, 208, 209, 210, 211, 212, 213, 214, 215, 216, 217, 218, 219, 220, 221, 222, 223, 224, and 225. In a further aspect a heterologous peptide has the amino acid sequence SAIKKPVT (SEQ ID NO:2) or TAIKKPVT (SEQ ID NO:3). In a further aspect a VLP displays a peptide of SEQ ID NO:2 and/or SEQ ID NO:3.

In certain aspects the heterolgous peptide is inserted in a coat polypeptide single-chain dimer of the VLP. The coat polypeptide single-chain dimer can comprise a first amino terminal coat polypeptide and a second carboxy terminal coat polypeptide. The heterologous peptide can be inserted in the A-B loop of the first, second, or first and second coat polypeptide. In certain aspects the heterologous peptide is inserted at an amino terminus of the first coat polypeptide or carboxy terminus of the second coat polypeptide.

In certain embodiments the bacteriophage VLP is a MS-2 VLP. The VLP composition can be formulated in a pharmaceutically acceptable formulation that can comprise an adjuvant, carrier, additive, and/or excipient. In certain aspects the formulation is a vaccine formulation.

Other embodiments are directed to immunogenic compositions comprising VLPs displaying one or more heterologous peptide selected from SEQ ID NO: 2-225.

Certain embodiments are directed to methods for stimulating an anti-malaria immunologic response in a subject comprising administering to the patient an effective amount of a composition described herein. In certain aspects the immunologic response is prophylactic and/or therapeutic. In certain aspects a subject administered an anti-malaria composition described herein is at risk of developing malaria, is diagnosed with malaria, or is infected with or has been exposed to *plasmodium*.

Certain aspects are directed to methods for treating a subject having a *plasmodium* infection comprising administering to the subject an effective amount of an anti-malaria composition described herein.

Certain embodiments are directed to methods of identifying a mimotope of a malaria peptide comprising contacting an RNA bacteriophage virus like particle (VLP) library displaying heterologous peptides with a monclonal antibody, which neutralizes malaria causing *plasmodium*, and isolating VLPs that specifically bind the monoclonal antibodies.

The term "treating" refers to both therapeutic (e.g., a lessening or amelioration of symptoms) treatment and prophylactic or preventative measures, wherein the object is to prevent or slow down (lessen) the targeted pathologic condition or disorder. Those in need of treatment include those already with the disorder or infection as well as those at risk of having the disorder or being infected, or those in whom the disorder or infection is to be prevented. In some embodiments, the subjects to be treated are human subjects suffering from or at risk of developing malaria. In some embodiments, the subjects to be treated are human subjects at risk for contracting malaria, including. The subjects to be treated may or may not have previously been infected by *plasmodium* or *P. falciparum* parasites.

The term "effective amount" for a therapeutic or prophylactic treatment refers to an amount or dosage of a composition sufficient to induce a desired response (e.g., an immunogenic response) in the individual to which it is administered. Preferably, the effective amount is sufficient to effect treatment, as defined above. The effective amount and method of administration of a particular therapeutic or prophylactic treatment may vary based on the individual patient and the stage of the disease, as well as other factors known to those of skill in the art. Therapeutic efficacy and toxicity of such compounds can be determined by standard pharmaceutical procedures in cell cultures or experimental animals, e.g., ED50 (the dose therapeutically effective in 50% of the population) and LD50 (the dose lethal to 50% of the population). The dose ratio of toxic to therapeutic effects is the therapeutic index, and it can be expressed as the ratio, LD50/ED50. Pharmaceutical compositions that exhibit large therapeutic indices are preferred.

As used herein, the term "antigen" is a molecule capable of being bound by an antibody or T-cell receptor. An antigen is additionally capable of inducing a humoral immune response and/or cellular immune response leading to the production of B- and/or T-lymphocytes. The structural aspect of an antigen, e.g., three-dimensional conformation or modification (e.g., phosphorylation), giving rise to a biological response is referred to herein as an "antigenic determinant" or "epitope." A peptide that mimics an epitope is referred to as a mimotope.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

FIG. 6 The amino acid sequence of RhS (SEQ ID NO: 4). Amino acids in bold show sites of similarity to the AIKK (SEQ ID NO: 227) motif identified in the 5A8 affinity selected VLPs.

FIG. 12A-12E List of the 200 most abundant first round 5A8 selections. Number at the left is the rank order of abundance of the peptide. Number at the right is the peptide length. (SEQ ID NOs 6 to 205).

DESCRIPTION

Figure 1:
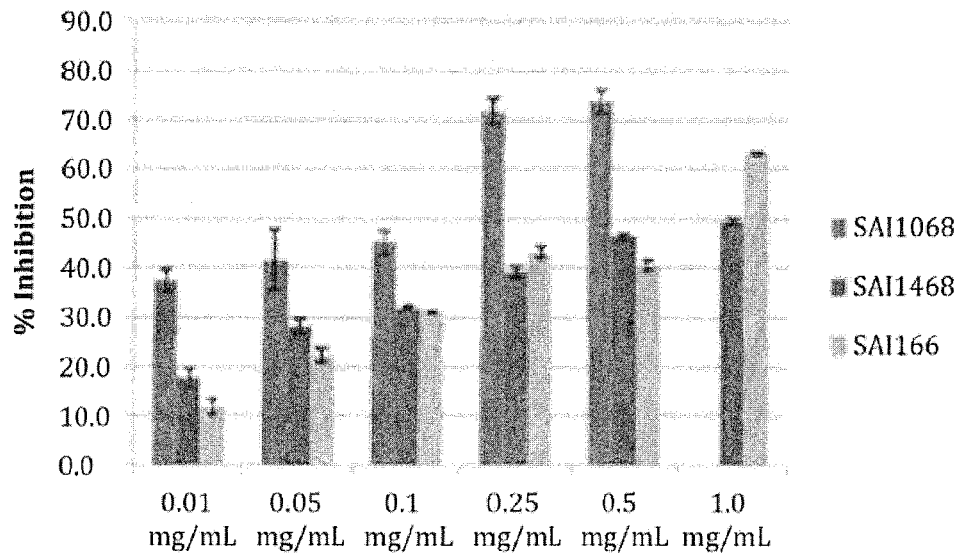
FIG. 1 GIA activity of polyclonal antibodies raised against full length rRH5 protein from different sources.

Malaria is widespread in tropical and subtropical regions. This includes much of Sub-Saharan Africa, Asia, and Latin America. The World Health Organization estimates that in 2012, there were 207 million cases of malaria that resulted in 473,000 and 789,000 deaths, many of whom were children in Africa. Malaria is a mosquito-borne infectious disease caused by parasitic protozoans. Malaria parasites belong to the genus *Plasmodium* (phylum Apicomplexa). In humans, malaria is caused by *P. falciparum, P. malariae, P. ovale, P. vivax*, and *P. knowlesi*. Among those infected, *P. falciparum* is the most common species identified (~75%) followed by *P. vivax* (~20%). The bite of an infected female mosquito introduces the parasites into a person's blood.

In the life cycle of *Plasmodium*, a motile infective sporozoite is transferred to a vertebrate host. A sporozoite travels through the blood vessels to the liver where it reproduces asexually producing thousands of merozoites. These infect red blood cells and initiate a series of asexual multiplication cycles that produce 8 to 24 new infective merozoites, at which point the cells burst and the infective cycle begins anew. Other merozoites develop into immature gametocytes, which are the precursors of male and female gametes. When a fertilized mosquito bites an infected person, gametocytes are taken up with the blood and mature in the mosquito gut. The male and female gametocytes fuse and form an ookinete—a fertilized, motile zygote. Ookinetes develop into new sporozoites that migrate to the insect's salivary glands, ready to infect a new vertebrate host. The sporozoites are injected into the skin, in the saliva, when the mosquito takes a subsequent blood meal. *Plasmodium* infection causes symptoms that include fever, fatigue, vomiting, and headaches. In severe cases it can cause yellow skin, seizures, coma, or death. Symptoms begin ten to fifteen days after being bitten. In those who have not been appropriately treated disease may recur months later.

Symptoms of malaria can recur after varying symptom-free periods. Depending upon the cause, recurrence can be classified as recrudescence, relapse, or reinfection. Recrudescence is when symptoms return after a symptom-free period. It is caused by parasites surviving in the blood as a result of inadequate or ineffective treatment. Relapse is when symptoms reappear after the parasites have been eliminated from blood but persist as dormant hypnozoites in liver cells. Relapse commonly occurs between 8-24 weeks and is commonly seen with *P. vivax* and *P. ovale* infections. Reinfection means the parasite that caused the past infection was eliminated from the body but a new parasite was introduced. Reinfection cannot readily be distinguished from recrudescence, although recurrence of infection within two weeks of treatment for the initial infection is typically attributed to treatment failure.

The risk of disease can be reduced by preventing mosquito bites by using mosquito nets and insect repellents, or with mosquito-control measures such as spraying insecticides and draining standing water. Several medications are available to prevent malaria in travellers to areas where the disease is common. Occasional doses of the medication sulfadoxine/pyrimethamine are recommended in infants and after the first trimester of pregnancy in areas with high rates of malaria. Despite a need, no effective vaccine exists. The recommended treatment for malaria is a combination of antimalarial medications that includes an artemisinin or quinine/doxycycline in combination with mefloquine, lumefantrine, or sulfadoxine/pyrimethamine.

I. Anti-Malaria Compositions

When expressed from a plasmid in bacteria, the coat protein of bacteriophage MS2 forms a virus-like particle (VLP), which has been adapted for peptide display and affinity-selection. Similar to other display systems, the MS2 VLP peptide display and affinity-selection platform comprises: (i) a surface-exposed site in a coat protein that tolerates insertions without disruption of coat protein folding or VLP assembly, and (ii) on encapsidation of a nucleic acid that encodes the coat protein and any guest peptide it displays. A single-chain dimer version of coat protein has been engineered. For examples of RNA bacteriophage libraries see PCT application PCT/US12/44206, PCT/US12/62073, and PCT/US13/20960, each of which is incorporated herein by reference in its entirety. Taking advantage of the close physical proximity of the N-terminus of one subunit to the C-terminus of the other, the coat coding sequence was duplicated and fused as a single reading frame. This yields a protein that is much more stable thermodynamically and tolerates foreign AB-loop insertions (Caldeira et al., *Vaccine*, 28(27):4384-4393, 2010; Peabody, *Arch Biochem Biophys*, 347(1):85-92, 1997; Peabody et al., *Nucleic Acids Res*, 24(12):2352-2359, 1996; Peabody et al., *J Mol Biol*, 380 (1):252-263, 2008).

The second requirement is satisfied by the VLP's ability to encapsidate the mRNA that encodes coat protein and any guest peptide it carries (Peabody et al., *J Mol Biol*, 380(1): 252-263, 2008). A complex library of random peptide sequences is constructed at the level of plasmid DNA (see FIG. 2 and Chackerian et al., *J Mol Biol*, 409(2):225-237, 2011). When the DNA is expressed, a corresponding library of VLPs is produced, which can then be subjected to affinity-selection. When the selecting agent is an antibody, selection yields VLPs displaying peptide mimics of the epitope the antibody recognizes. The affinity-selection procedure is schematically illustrated in FIG. 3. Normally, several iterative rounds of selection are needed to obtain a relatively simple population of peptides that tightly bind the target antibody.

Each VLP normally displays 90 copies of a heterologous peptide. At such high valencies avidity effects limit selection stringency. To find the tightest binding peptides, display valency is reduced, usually at round 3. This is accomplished through the use of a variant of pDSP62(am), which contains an amber codon at the junction between the two halves of the single-chain dimer, so in the presence of a weak suppressor tRNA (expressed from a second, compatible plasmid) about 3% of coat protein takes the form of the single-chain dimer with a foreign peptide in its downstream AB-loop. This co-assembles with an excess of the normally terminated wild-type protein to form mosaic capsids. Both forms of the protein are produced from a single mRNA, which is packaged by the VLP, thus preserving the genotype/phenotype linkage essential for affinity selection. Typically, selection is performed in two rounds at high valency, followed by two additional rounds at low valency. This usually results in a simple population of one or more sequence families, depending on the binding preferences of the selecting antibody. After selection, the selected sequences are returned to high valency (and high immunogenicity) by cloning into pDSP62.

Full-length recombinant RH5 protein from various expression platforms can achieve up to ~75% protection in in vitro growth inhibition assays (GIA), where inhibition of parasite invasion into red blood cells conferred by addition of antibody/serum can be assessed (FIG. 1 and Ord et al., *PLos One,* 7(1):e30251, 2012). Using recombinant RH5 antigen, monoclonal antibodies (mAbs) have been developed against *P. falciparum* RH5. These mAbs were tested for their ability to neutralize parasite growth in vitro using GIA. Results from the preliminary GIA with hybridoma supernatants identified 25 mAbs with varying degrees of neutralizing activity. In subsequent GIA studies using purified mAbs, 3 mAbs were identified with >95% growth inhibitory activity. The 3 most active mAbs were capable of blocking parasite growth nearly 100% at a concentration of 0.1 mg/ml, in contrast to the 50-75% inhibition attained by polyclonal antiserum at a concentration of 0.5 mg/ml. Since polyclonal antibody represents the sum of antibodies made against many epitopes on RH5, it requires larger amount of antibodies to achieve higher levels of inhibition. Therefore, the most parsimonious means of directing the immune response to these critical epitopes corresponding to the mAbs and avoiding any decoy or masking epitopes would be developing a vaccine to the epitope(s). 5A8 monoclonal antibodies were used to affinity-select VLPs displaying peptides from random sequence libraries. The VLPs were tested for their ability to elicit antibodies in mice that efficiently inhibited parasite invasion of erythrocytes in vitro. These peptide-displaying VLPs are candidates for malaria vaccines.

In certain aspects anti-malaria compositions comprise one or more VLPs comprising heterologous peptide(s) (SEQ ID NO:2, 3, and/or 6 to 205) representing malaria epitope(s). VLPs comprising one or more malaria epitopes can be administered to a subject to stimulate or induce an anti-malaria immune response. In certain aspects the malaria VLPs can be in a pharmaceutically acceptable, carrier, additive, and/or excipient. In certain aspects a subject is in need of such treatment in that the subject is at risk for developing malaria (e.g. is traveling to or is located in an area that is endemic for malaria), or the subject is identified as being exposed to or infected by the microbial agents that cause malaria, or the subject has contracted malaria. In a further aspect the subject may wish to boost his/her immune system against a dormant infection to attenuate any subsequent active infection or more aggressive infection.

Certain embodiments are directed to anti-malaria compositions comprising VLPs displaying heterologous malaria epitopes. These epitopes can be identified by affinity selection methods. In certain aspects anti-malaria compositions can be used to stimulate or induce immunity to anti-malaria VLPs and *plasmodium*. Anti-malaria compositions can be administered to a subject in need of prophylactic or therapeutic treatment for malaria. In certain aspects the anti-malaria compositions may be administer by parenteral administration (e.g., intramuscularly or intravenously). Anti-malaria composition can comprise a population of immunogenic VLPs.

Other embodiments are directed to prophylactic or therapeutic methods. Certain aspects are directed to methods of reducing the likelihood of a subsequent malaria infection, or reducing the likelihood that a dormant infection will become fully infective or that a low-grade infection will become higher grade or aggressive infection.

The exact dosage is chosen by the individual physician in view of the patient to be treated. Dosage and administration are adjusted to provide sufficient levels of the active moiety or to maintain the desired effect. Additional factors that may be taken into account include the prevalence of *P. falciparum* in the geographical vicinity of the patient, the severity of the disease state of the patient, age, and weight of the patient; diet, time and frequency of administration, drug combination(s), reaction sensitivities, and tolerance/response to therapy. An appropriate effective amount can be readily determined using only routine experimentation. Several doses may be needed per individual in order to achieve a sufficient response to effect treatment. Suitable regimes for initial administration and follow-up administration (e.g., booster shots) are also variable, but are typified by an initial administration followed in intervals (weeks or months) by a subsequent administration.

III. Pharmaceutical Compositions

In light of the current description, the determination of an appropriate treatment regimen (e.g., dosage, frequency of administration, etc.) is within the skill of the art. For administration, the components described herein will be formulated in a unit dosage form in association with a pharmaceutically acceptable carrier. Such vehicles are usually nontoxic and non-therapeutic. Examples of such vehicles are water, saline, Ringer's solution, dextrose solution, and Hank's solution. Non-aqueous vehicles such as fixed oils and ethyl oleate may also be used. A preferred vehicle is 5% (w/w) human albumin in saline. The vehicle may contain minor amounts of additives, such as substances that enhance isotonicity and chemical stability, e.g., buffers and preservatives.

The compositions described herein can be administered independently or in combination by any suitable route. Examples of parenteral administration include intravenous, intraarterial, intramuscular, intraperitoneal, and the like. The routes of administration described herein are merely an example and in no way limiting.

The dose of the compositions administered to an animal, particularly in a human, in accordance with embodiments of the invention, should be sufficient to result in a desired response in the subject over a reasonable time frame. It is known that the dosage of immunogenic compositions depends upon a variety of factors, including the effectiveness of the immunogenic composition employed, the age, species, condition or disease state, and/or body weight of the subject.

Moreover, dose and dosage regimen, will depend mainly on the type of biological damage to the host, the type of subject, the history of the subject, and the type of composition being administered. The dose will be determined by route, timing, and frequency of administration, as well as the existence, nature, and extent of any adverse side effects that might accompany the administration of a particular composition and the desired physiological effect. It is also known that various conditions or disease states, in particular, chronic conditions or disease states, may require prolonged treatment involving multiple administrations. If multiple doses are employed, the frequency of administration will depend, for example, on the type of subject. One skilled in the art can ascertain upon routine experimentation the appropriate route and frequency of administration in a given subject that are most effective. Suitable doses and dosage regimens can be determined by conventionally known range-finding techniques.

The immunogenic compositions for use in embodiments of the invention generally include carriers. These carriers may be any of those conventionally used and are limited only by the route of administration and chemical and physical considerations, such as solubility. In addition, the composition may be formulated as polymeric compositions, inclusion complexes, such as cyclodextrin inclusion complexes, liposomes, microspheres, microcapsules, and the like, without limitation.

The pharmaceutically acceptable excipients described herein, for example, vehicles, adjuvants, carriers, or diluents, are well known and readily available. It is preferred that the pharmaceutically acceptable carrier be one which is chemically inert with respect to the therapeutic composition and one that has no detrimental side effects or toxicity under the conditions of use.

The choice of excipient will be determined, in part, by the particular composition, as well as by the particular method used to administer the composition. Accordingly, there are a wide variety of suitable formulations of the pharmaceutical composition used in the embodiments that are described herein. For example, the non-limiting formulations can be injectable formulations such as, but not limited to, those for intravenous, subcutaneous, intramuscular, or intraperitoneal injection. Non-limiting formulations suitable for parenteral administration include aqueous and non-aqueous isotonic sterile injection solutions, including non-active ingredients such as antioxidants, buffers, bacteriostats, solubilizers, thickening agents, stabilizers, preservatives, surfactants, and the like. The solutions can include oils, fatty acids, including detergents and the like, as well as other well known and common ingredients in such compositions, without limitation.

IV. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Affinity-Selection on MS2 VLPs

Affinity selections were performed using a monoclonal antibody (5A8) that was chosen for: (1) its ability to recognize the Rh5 protein of *Plasmodium faliciparum*, and (2) for its ability to inhibit parasite invasion and/or growth in an in vitro Growth Inhibitory Assay (GIA). VLPs displaying mimics of the epitopes recognized by these antibodies were selected to produce vaccines able to elicit antibodies that recognize Rh5 and inhibit *P. faliciparum* infection. Herein is described the identification of such mimics and show that they can elicit the desired antibody responses in immunized mice.

Figure 2:
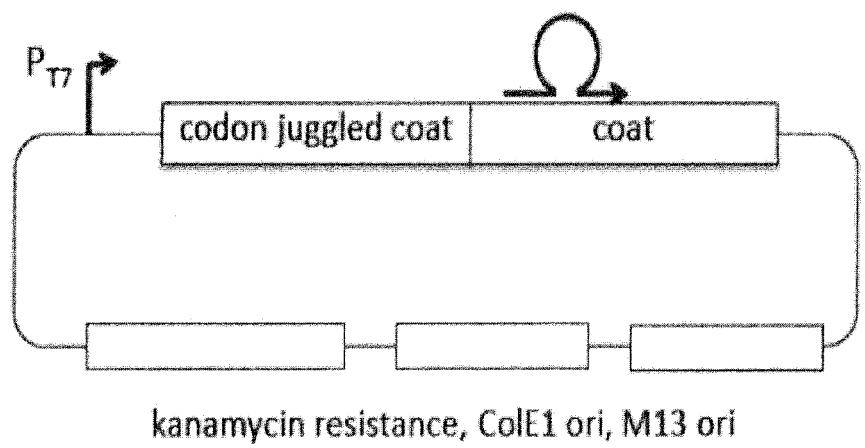
FIG. 2 The structure of pDSP62, the vector used for library construction on MS2 VLPs. Insertions are created by primer extension on a single-stranded, dUTP-substituted, circular template. Closed circular DNA is then electroporated into *E. coli*. Expression of the recombinant coat protein yields VLP libraries.
Figure 3:
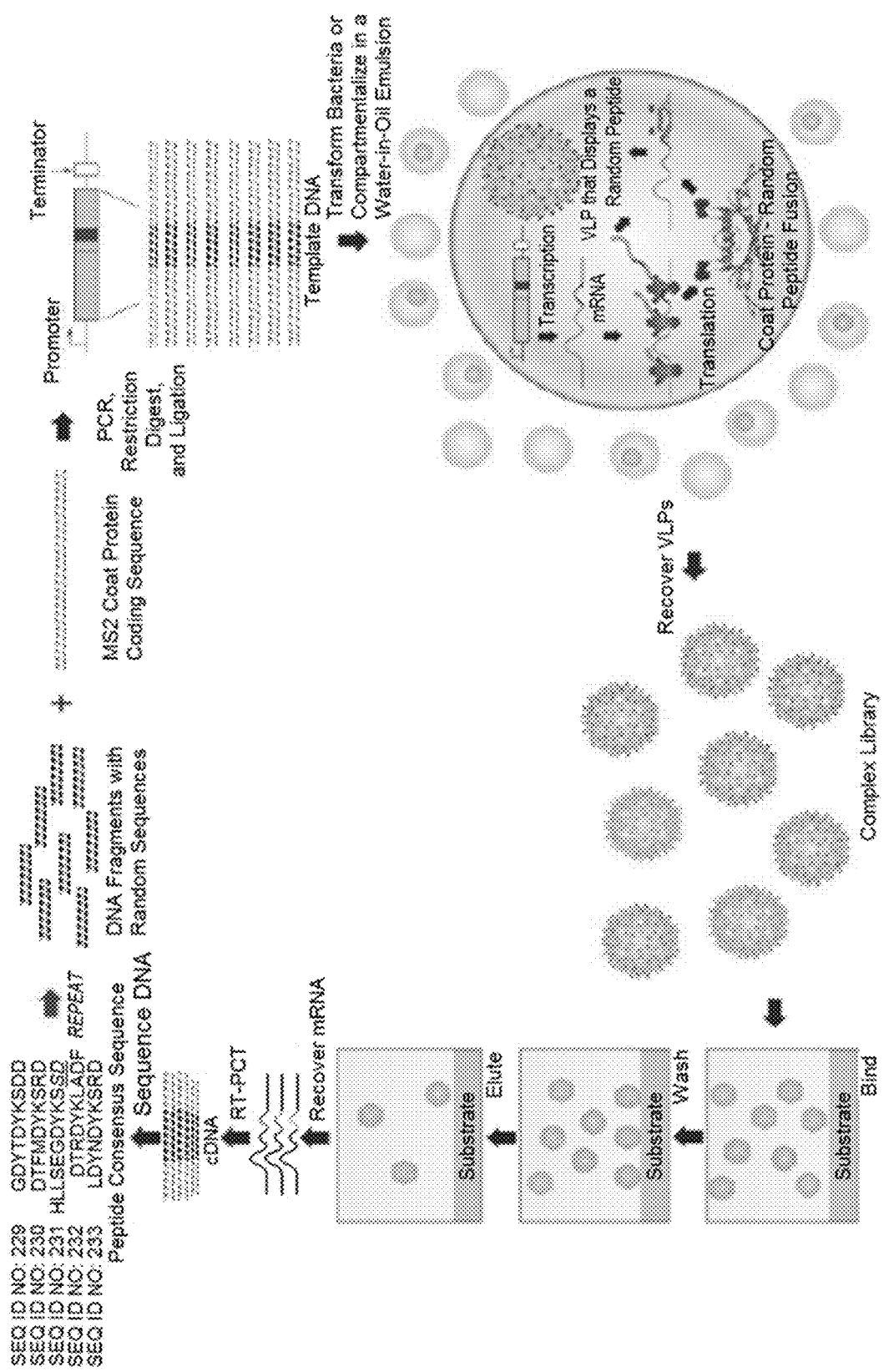
FIG. 3 Library construction and affinity selection using MS2 VLPs. A library of template DNA molecules encoding the single-chain dimer with random peptide sequences inserted into the down stream AB-loop is produced. Expression in *E. coli* yields corresponding library of MS2 VLPs, which is subjected to affinity selection. After washing, VLPs displaying peptides with an affinity for the mAb are eluted and then subjected to RT-PCR to generate cDNA for another round of selection.
Figure 4:
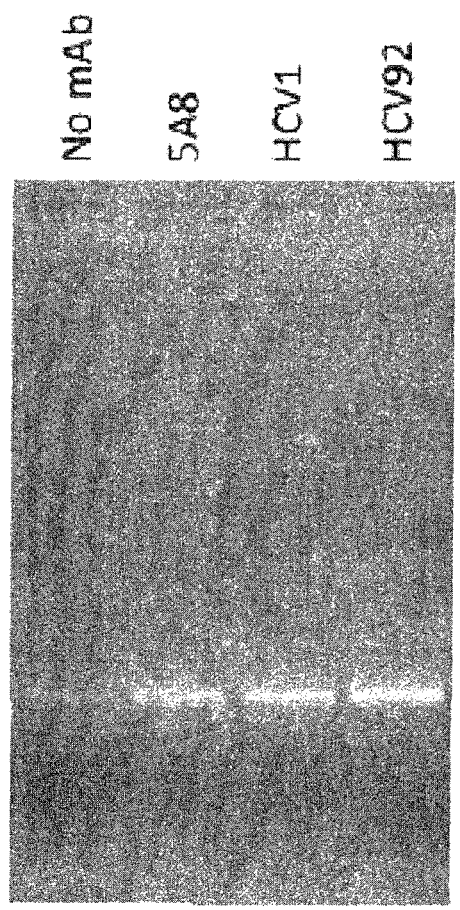
FIG. 4 PCR products obtained after affinity selections using the indicated mAbs.
Figure 5:
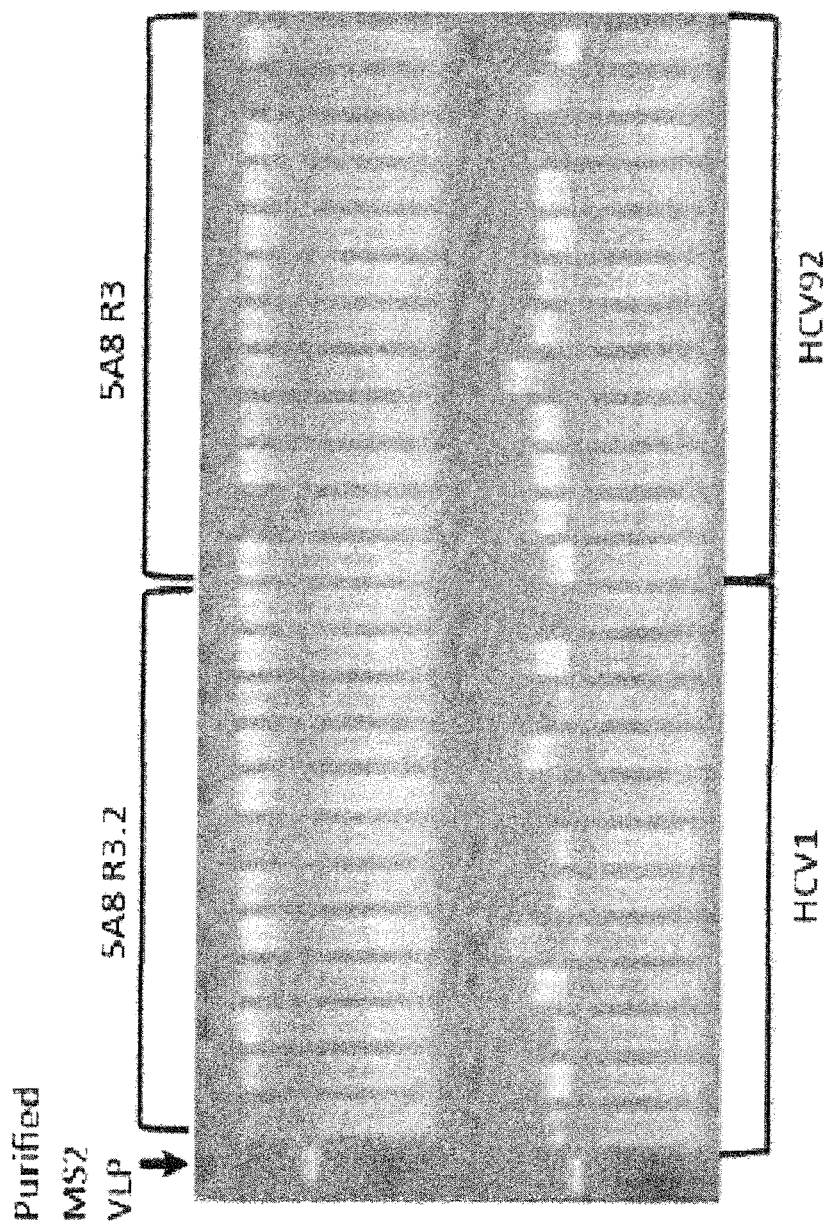
FIG. 5 Agarose gel electrophoresis of cell lysates containing VLPs selected by the indicated mAbs. The gel is stained with ethidium bromide, allowing VLPs to be visualized by the RNA they contain. The fact running smear in each sample is cellular nucleic acids. R3.2 and R3 refer respectively to the round 3 products of the two independent 5A8 selections. HCV1 and HCV92 are mAbs that recognize hepatitis C virus and are included for comparison.
Figure 7:
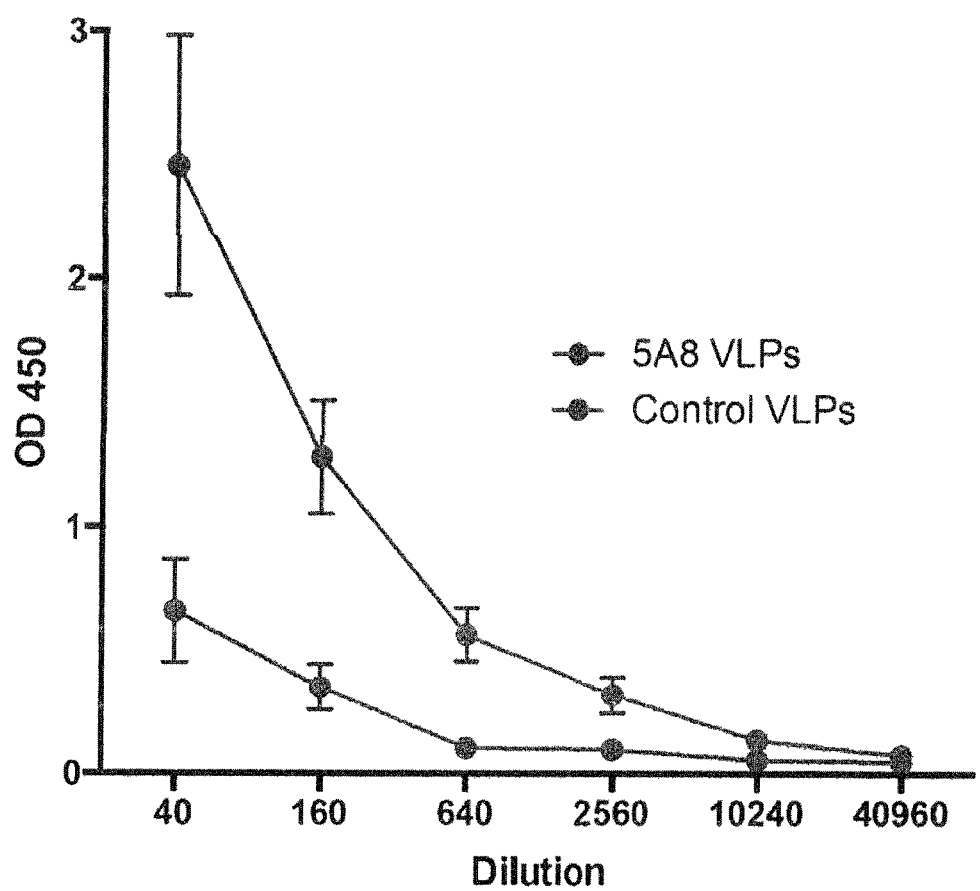
FIG. 7 ELISA reactivity of sera from mice immunized with the 5A8 VLP selectant for reaction with recombinant RH5 protein. SAIKKPVTGGGGC (SEQ ID NO:5).

Selections were conducted by biopanning using four large random sequence libraries (each ~$10^{10}$ individual members) of 6mers, 7mers, 8mers, and 10mers constructed in the plasmid vector pDSP62 (FIG. 2 and Chackerian et al., *J Mol Biol*, 409(2):225-237, 2011). Two entirely independent selections were conducted using the 5A8 monoclonal antibody. In each case, two rounds were conducted at high valency, and a third was performed at low valency to increase selection stringency. Biopanning was conducted by first adsorbing 500 ng of the antibody to 2 or 3 wells of an immulon microtiter plate. The VLP library mixture was added to the wells, incubated for 2 hours, and, after extensive washing, the bound VLPs were eluted in glycine buffer at pH2.7. The RNA they contained was subjected to reverse transcription and PCR. FIG. 4 shows a typical result. The PCR product from the $1^{st}$ round was re-cloned in pDSP62, VLPs were produced, and employed in a second round of selection. The PCR products of the $2^{nd}$ round were cloned in pDSP62(am) for low valency display, and the resulting VLPs were subjected to a 3rd selection round. The round 3 products from both 5A8 selections were then cloned again in pDSP62, returning them to high display valency, and the VLPs produced by 24 individual clones (12 from each of the 2 selections) were characterized by electrophoresis on agarose gel (FIG. 5).

The round 3 selectants all showed the same electrophoretic mobility, suggesting a highly restricted population had already been obtained. The twelve round 2 selections were sequenced in addition to eight taken from round 3. All twelve round 2 selections displayed a peptide of sequence, SAIKKPVT (SEQ ID NO:2). Seven of eight round 3 selections also displayed the SAIKKPVT (SEQ ID NO:2) peptide, and another had the sequence TAIKKPVT (SEQ ID NO:3). The presence of two lysines in the peptide explains the greatly reduced mobility they show upon electrophoresis.

The first round 5A8 selections were subjected to deep sequence analysis. The 200 most abundant sequences (from a total of about 2,500) were analyzed by ClustalW2 alignment. It should be emphasized that after a single selection round the peptide population is highly complex and still contains mostly irrelevant (i.e. probable non-antibody-binding) sequences. Interestingly, SAIKKPVT (SEQ ID NO:2) was not the most abundant sequence encountered in round 1, or even the most abundant member of its own sequence family. The three most abundant members of the SAIKKPVT (SEQ ID NO:2) family include VAIKRPGKGT (SEQ ID NO:188) (168 occurrences, 13th most abundant sequence), SAIKKPVT (SEQ ID NO:2) (92 occurrences, 42nd most abundant sequence), TAIKKMKS (SEQ ID NO:187) (52 occurrences, 130th most abundant sequence). The conserved elements are fairly obvious. Each sequence contains the AIK(K/R) motif. Scanning the whole collection revealed a number of other peptides (each occurring only once) that matched AIK(K/R) including SAIKKPVA (SEQ ID NO:206), TAIKKKKS (SEQ ID NO:207), TAIKKMES (SEQ ID NO:208), TAIKKMKP (SEQ ID NO:209), TAIKKMKY (SEQ ID NO:210), TAIKKRT (SEQ ID NO:211), YAIKKPVT (SEQ ID NO:212), VAIKRPGRGT (SEQ ID NO:213), VAIKRPFEFT (SEQ ID NO:214), VAIKRP (SEQ ID NO:215), VAIKPARQGT (SEQ ID NO:216), TAIKKRT (SEQ ID NO:217), TAIKKMKY (SEQ ID NO:218), TAIKKMKP (SEQ ID NO:219), TAIKKMES (SEQ ID NO:220), TAIKKKS (SEQ ID NO:221), SAIKKPVA (SEQ ID NO:222), GAIKRPGKGT (SEQ ID NO:223), AAIKRPGKGT (SEQ ID NO:224), and YAIKKPVT (SEQ ID NO:225), many of which show additional similarities to one another outside this core motif. It is interesting that not only is the core sequence conserved, but also its relative position in the peptide. The AIK(K/R) always occupies amino acids 2-5 (from the amino terminal end).

The relatively large number of occurrences of AIK(K/R), the fact that the core sequence happens to match a sequence in the Rh5 antigen, the rapid convergence of the selection upon a single sequence by the second round, and the observation that VLPs with the SAIKKPVT (SEQ ID NO:2) strongly bind the 5A8 antibody suggest that a relevant epitope ahs been identified. The SAIKKPVT (SEQ ID NO:2) sequence contains a 4-amino acid identity to the AIKK (SEQ ID NO:227) peptide near the RH5 N-terminus.

Figure 8A:
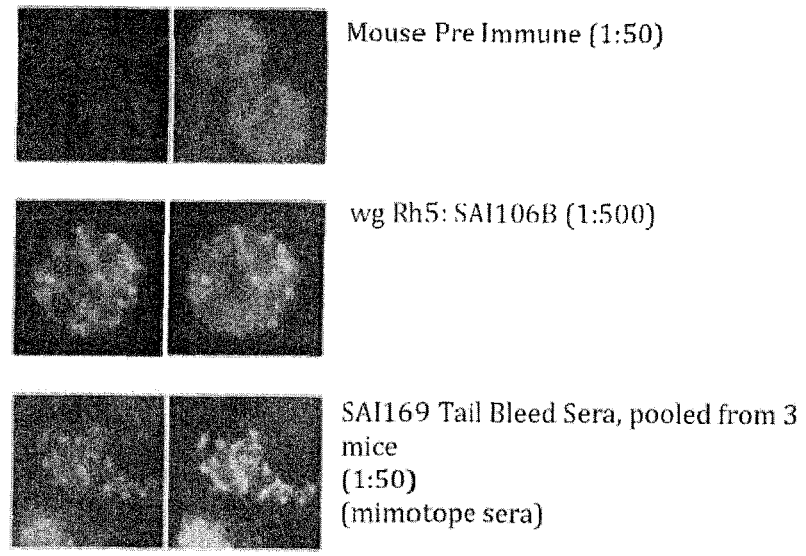
FIG. 8 Mice immunized with the 5A8-selected VIP make antibodies that recognize the Rh5 protein on schizonts (8A) and on Western blot (8B).
Figure 8B:
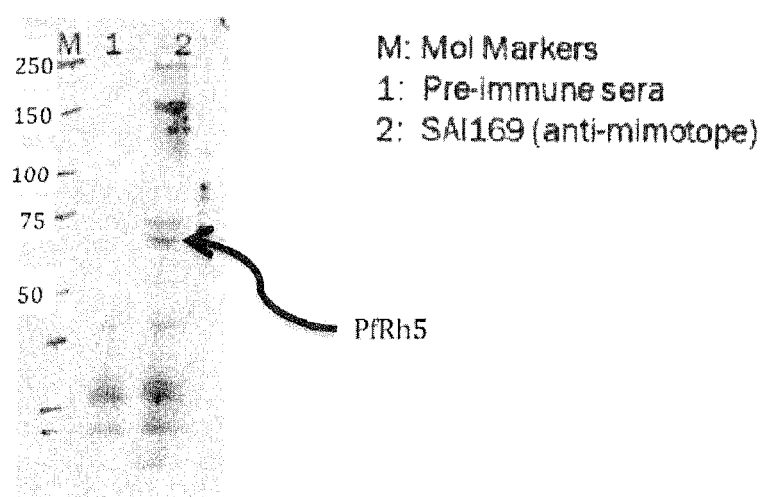
Figure 9:
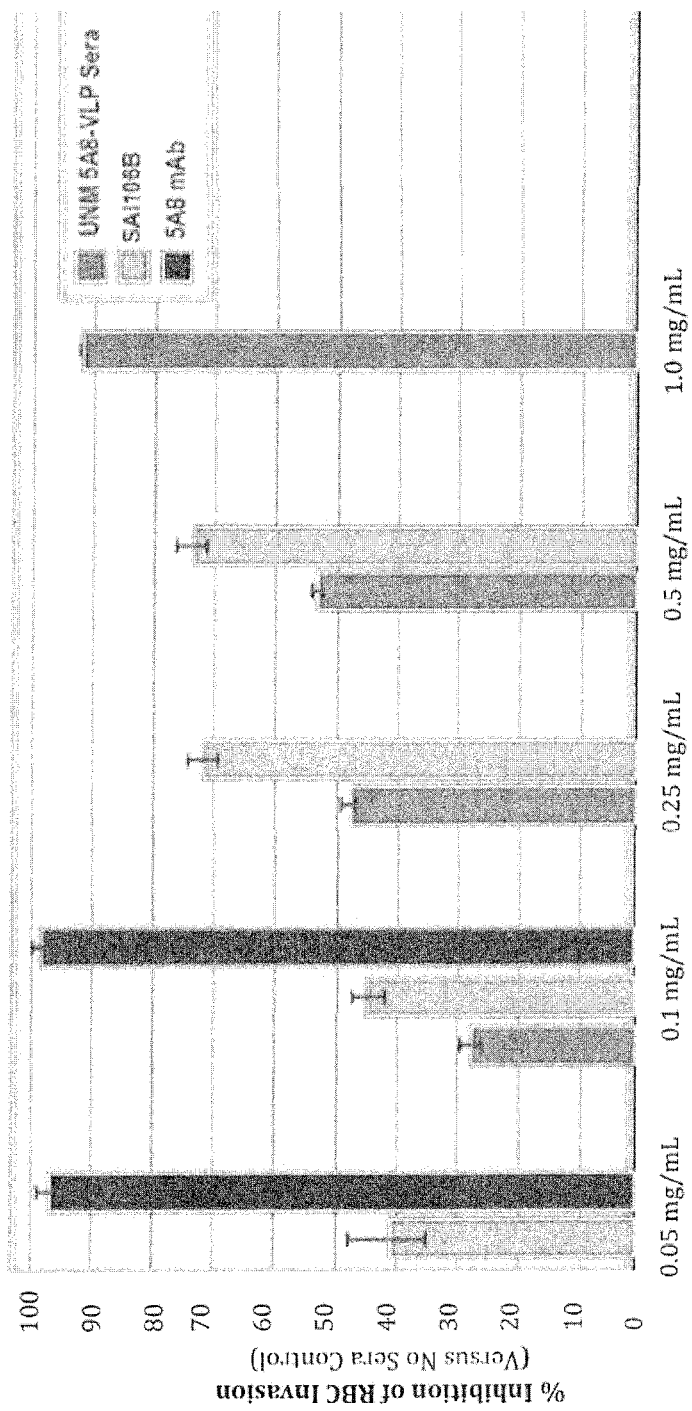
FIG. 9 Anti 5A8-VLP serum shows >90% GIA activity at 1 mg/ml on 3D7 parasites.
Figure 10:
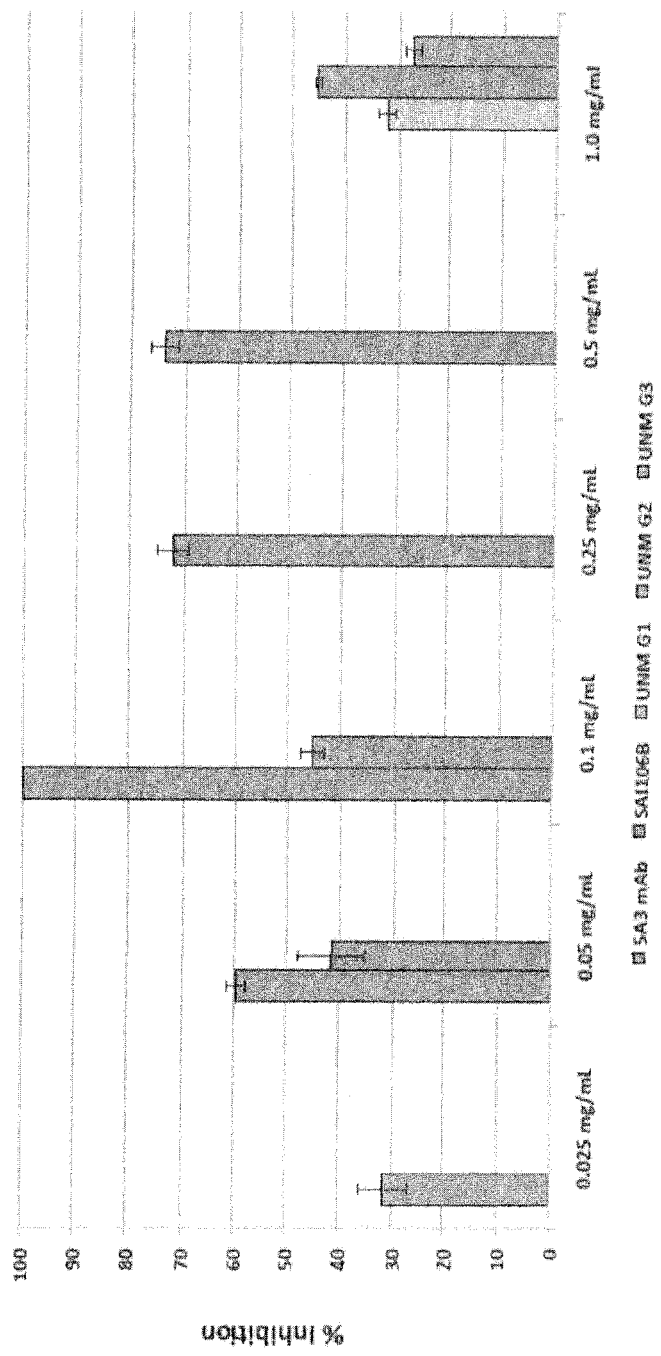
FIG. 10 Anti-5A3 and 2E11 mimotope polyclonal mouse serum achieves 27-45% GIA activity at 1 mg/ml; on 3D7 parasites.
Figure 11:
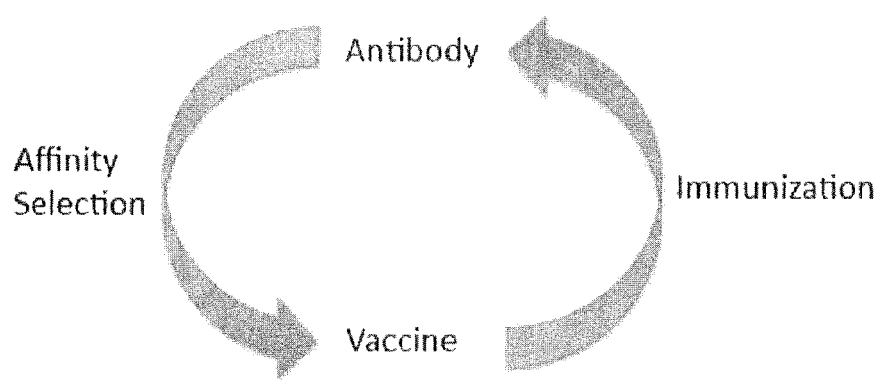
FIG. 11 Illustration of the vaccine discovery loop—use of an antibody to affinity select peptide-VLPs able to elicit antibodies with activities like that of the selecting antibody.

VLP purifications, ELISA, and immunization of mice. The 5A8 VLP selections described above were purified by chromatography on Sepharose CL4B. The selected VLPs were tested for the ability to bind 5A8 in direct ELISA (FIGS. 8A and 8B). Strong reaction with 5A8 (the selecting antibody) was observed, but reaction with control antibodies was not detected.

Immunization with the 5A8 selection and generation of anti-peptide antibodies. Four mice were immunized with VLP displaying the SAIKKPVT (SEQ ID NO:2) sequence. Injections were i.m. with 5 μg of VLP, 3 times at 2 week intervals. All immunizations were performed using the GLA-SE adjuvant (Infectious Disease Research Institute, Seattle Wash.) according to recommendations provided by SAIC. To assess the relative anti-RH5 antibody titers of the antisera, reactivity of sera to recombinant RH5 was determined by ELISA (FIG. 7). All of the mice immunized with 5A8 VLPs elicited high-titer antibodies against RH5 protein.

Reaction of the antisera with authentic Rh5 was tested by two means. First the antiserum was able to detect the presence of Rh5 in schizonts by immunofluorescence, and by western blot of proteins extracted from schizonts (FIGS. 8A and 8B). Most importantly, the anti-5A8-VLP antiserum was active in GIA, showing greater than 90% inhibition at 1 mg/ml IgG concentration (FIG. 9). Remembering that only a small fraction of the total IgG is likely to be specific for the 5A8 epitope, this level of inhibition is impressive.

What is claimed is:

1. A composition comprising a virus like particle (VLP) displaying a heterologous peptide insertion of 4 to 40 amino acids comprising an amino acid sequence of AIKX$_{KR}$ where X$_{KR}$ is K or R (SEQ ID NO: 226).

2. The composition of claim 1, wherein the heterologous peptide has a consensus sequence of (X)$_n$AIKX$_{KR}$(X)$_m$ (SEQ ID NO:4) wherein X is any amino acid, n is 0 to 20, and m is 0 to 20 and X$_{KR}$ is K or R.

3. The composition of claim 1, wherein the heterologous peptide has the amino acid sequence selected from SEQ ID NO:2, 3, 5, 187, 188, 206, 207, 208, 209, 210, 211, 212, 213, 214, 215, 217, 218, 219, 220, 221, 222, 223, 224, or 225.

4. The composition of claim 1, wherein the heterologous peptide has the amino acid sequence of SEQ ID NO:2 or SEQ ID NO:3.

5. The composition of claim 1, wherein the VLP is a RNA bacteriophage VLP.

6. The composition of claim 1, wherein the RNA bacteriophage VLP is a MS2 VLP.

7. The composition of claim 1, further comprising a pharmaceutically acceptable adjuvant, carrier, additive, or excipient.

8. The composition of claim 4, wherein the heterolgous peptide is inserted in a coat polypeptide of the bacteriophage VLP.

9. The composition of claim 8 wherein the coat polypeptide is a single-chain dimer coat polypeptide, wherein the coat polypeptide single chain dimer comprises a first amino terminal coat polypeptide and a second carboxy terminal coat polypeptide.

10. The composition of claim 9 wherein the heterologous peptide is inserted in an A-B loop of the first, the second, or the first and the second coat polypeptide of the coat polypeptide single-chain dimer.

11. The composition of claim 9, wherein the heterologous peptide is inserted at an amino terminus of the first coat polypeptide or carboxy terminus of the second coat polypeptide.

12. A composition comprising a bacteriophage virus like particle (VLP) displaying a heterologous peptide selected from a peptide having the sequence SEQ ID NO:2, 3, 5, 187, 188, 206, 207, 208, 209, 210, 211, 212, 213, 214, 215, 217, 218, 219, 220, 221, 222, 223, 224, or 225.

13. A method for stimulating an anti-malaria immunologic response in a subject comprising administering to the patient an effective amount of a composition of claim 1.

14. A method for treating a subject having a plasmodium infection comprising administering to the subject an effective amount of a composition of claim 1.

* * * * *

SEQUENCE LISTING

<160> NUMBER OF SEQ ID NOS: 233

<210> SEQ ID NO 1
<211> LENGTH: 503
<212> TYPE: PRT
<213> ORGANISM: Plasmodium falciparum

<400> SEQUENCE: 1

Met Phe Glu Asn Ala Ile Lys Lys Thr Lys Asn Gln Glu Asn Asn Leu
1 5 10 15

Thr Leu Leu Pro Ile Lys Ser Thr Glu Glu Glu Lys Asp Asp Ile Lys
20 25 30

Asn Gly Lys Asp Ile Lys Lys Glu Ile Asp Asn Asp Lys Glu Asn Ile
35 40 45

Lys Thr Asn Asn Ala Lys Asp His Ser Thr Tyr Ile Lys Ser Tyr Leu
50 55 60

Asn Thr Asn Val Asn Asp Gly Leu Lys Tyr Leu Phe Ile Pro Ser His
65 70 75 80

Asn Ser Phe Ile Lys Lys Tyr Ser Val Phe Asn Gln Ile Asn Asp Gly
85 90 95

Met Leu Leu Asn Glu Lys Asn Asp Val Lys Asn Asn Glu Asp Tyr Lys
100 105 110

Asn Val Asp Tyr Lys Asn Val Asn Phe Leu Gln Tyr His Phe Lys Glu
115 120 125

Leu Ser Asn Tyr Asn Ile Ala Asn Ser Ile Asp Ile Leu Gln Glu Lys
130 135 140

Glu Gly His Leu Asp Phe Val Ile Ile Pro His Tyr Thr Phe Leu Asp
145 150 155 160

Tyr Tyr Lys His Leu Ser Tyr Asn Ser Ile Tyr His Lys Ser Ser Thr
165 170 175

-continued

```
Tyr Gly Lys Cys Ile Ala Val Asp Ala Phe Ile Lys Lys Ile Asn Glu
            180                 185                 190
Thr Tyr Asp Lys Val Lys Ser Lys Cys Asn Asp Ile Lys Asn Asp Leu
            195                 200                 205
Ile Ala Thr Ile Lys Lys Leu Glu His Pro Tyr Asp Ile Asn Asn Lys
210                 215                 220
Asn Asp Asp Ser Tyr Arg Tyr Asp Ile Ser Glu Ile Asp Asp Lys
225                 230                 235                 240
Ser Glu Glu Thr Asp Asp Glu Thr Glu Val Glu Asp Ser Ile Gln
                245                 250                 255
Asp Thr Asp Ser Asn His Thr Pro Ser Asn Lys Lys Asn Asp Leu
            260                 265                 270
Met Asn Arg Thr Phe Lys Lys Met Met Asp Glu Tyr Asn Thr Lys Lys
            275                 280                 285
Lys Leu Ile Lys Cys Ile Lys Asn His Glu Asn Asp Phe Asn Lys
            290                 295                 300
Ile Cys Met Asp Met Lys Asn Tyr Gly Thr Asn Leu Phe Glu Gln Leu
305                 310                 315                 320
Ser Cys Tyr Asn Asn Phe Cys Asn Thr Asn Gly Ile Arg Tyr His
                325                 330                 335
Tyr Asp Glu Tyr Ile His Lys Leu Ile Leu Ser Val Lys Ser Lys Asn
            340                 345                 350
Leu Asn Lys Asp Leu Ser Asp Met Thr Asn Ile Leu Gln Gln Ser Glu
            355                 360                 365
Leu Leu Leu Thr Asn Leu Asn Lys Lys Met Gly Ser Tyr Ile Tyr Ile
            370                 375                 380
Asp Thr Ile Lys Phe Ile His Lys Glu Met Lys His Ile Phe Asn Arg
385                 390                 395                 400
Ile Glu Tyr His Thr Lys Ile Ile Asn Asp Lys Thr Lys Ile Ile Gln
                405                 410                 415
Asp Lys Ile Lys Leu Asn Ile Trp Arg Thr Phe Gln Lys Asp Glu Leu
            420                 425                 430
Leu Lys Arg Ile Leu Asp Met Ser Asn Glu Tyr Ser Leu Phe Ile Thr
            435                 440                 445
Ser Asp His Leu Arg Gln Met Leu Tyr Asn Thr Phe Tyr Ser Lys Glu
450                 455                 460
Lys His Leu Asn Asn Ile Phe His His Leu Ile Tyr Val Leu Gln Met
465                 470                 475                 480
Lys Phe Asn Asp Val Pro Ile Lys Met Glu Tyr Phe Gln Thr Tyr Lys
                485                 490                 495
Lys Asn Lys Pro Leu Thr Gln
            500
```

<210> SEQ ID NO 2
<211> LENGTH: 8
<212> TYPE: PRT
<213> ORGANISM: artificial sequence
<220> FEATURE:
<223> OTHER INFORMATION: synthetic peptide

<400> SEQUENCE: 2

```
Ser Ala Ile Lys Lys Pro Val Thr
1               5
```

<210> SEQ ID NO 3

```
<211> LENGTH: 8
<212> TYPE: PRT
<213> ORGANISM: artificial sequence
<220> FEATURE:
<223> OTHER INFORMATION: synthetic peptide

<400> SEQUENCE: 3

Thr Ala Ile Lys Lys Pro Val Thr
1               5

<210> SEQ ID NO 4
<211> LENGTH: 6
<212> TYPE: PRT
<213> ORGANISM: artificial sequence
<220> FEATURE:
<223> OTHER INFORMATION: synthetic peptide
<220> FEATURE:
<221> NAME/KEY: misc_feature
<222> LOCATION: (1)..(1)
<223> OTHER INFORMATION: Xaa is any amino acid in a sequence 0 to 36
      amino acids in length
<220> FEATURE:
<221> NAME/KEY: misc_feature
<222> LOCATION: (5)..(5)
<223> OTHER INFORMATION: Xaa can be either Lys or Arg
<220> FEATURE:
<221> NAME/KEY: misc_feature
<222> LOCATION: (6)..(6)
<223> OTHER INFORMATION: Xaa is any amino acid in a sequence 0 to 36
      amino acids in length

<400> SEQUENCE: 4

Xaa Ala Ile Lys Xaa Xaa
1               5

<210> SEQ ID NO 5
<211> LENGTH: 13
<212> TYPE: PRT
<213> ORGANISM: artificial sequence
<220> FEATURE:
<223> OTHER INFORMATION: synthetic peptide

<400> SEQUENCE: 5

Ser Ala Ile Lys Lys Pro Val Thr Gly Gly Gly Gly Cys
1               5                   10

<210> SEQ ID NO 6
<211> LENGTH: 7
<212> TYPE: PRT
<213> ORGANISM: artificial sequence
<220> FEATURE:
<223> OTHER INFORMATION: synthetic peptide

<400> SEQUENCE: 6

Leu Ser Gly Gly Trp Pro Glu
1               5

<210> SEQ ID NO 7
<211> LENGTH: 8
<212> TYPE: PRT
<213> ORGANISM: artificial sequence
<220> FEATURE:
<223> OTHER INFORMATION: synthetic peptide

<400> SEQUENCE: 7

Leu Ser Gly Gly Trp Pro Glu Gly
1               5

<210> SEQ ID NO 8
```

```
<211> LENGTH: 7
<212> TYPE: PRT
<213> ORGANISM: artificial sequence
<220> FEATURE:
<223> OTHER INFORMATION: synthetic peptide

<400> SEQUENCE: 8

Leu Leu Asp Ser Gly Gln Trp
1               5

<210> SEQ ID NO 9
<211> LENGTH: 6
<212> TYPE: PRT
<213> ORGANISM: artificial sequence
<220> FEATURE:
<223> OTHER INFORMATION: synthetic peptide

<400> SEQUENCE: 9

Leu Arg Asp Ala Asn Pro
1               5

<210> SEQ ID NO 10
<211> LENGTH: 9
<212> TYPE: PRT
<213> ORGANISM: artificial sequence
<220> FEATURE:
<223> OTHER INFORMATION: synthetic peptide

<400> SEQUENCE: 10

Gly Gln Lys Leu Gly Asp Ile Gln Glu
1               5

<210> SEQ ID NO 11
<211> LENGTH: 8
<212> TYPE: PRT
<213> ORGANISM: artificial sequence
<220> FEATURE:
<223> OTHER INFORMATION: synthetic peptide

<400> SEQUENCE: 11

Trp Thr Thr Gly Gly Pro Thr His
1               5

<210> SEQ ID NO 12
<211> LENGTH: 8
<212> TYPE: PRT
<213> ORGANISM: artificial sequence
<220> FEATURE:
<223> OTHER INFORMATION: synthetic peptide

<400> SEQUENCE: 12

Arg Trp Pro Thr Gly Ala Pro Cys
1               5

<210> SEQ ID NO 13
<211> LENGTH: 7
<212> TYPE: PRT
<213> ORGANISM: artificial sequence
<220> FEATURE:
<223> OTHER INFORMATION: synthetic peptide

<400> SEQUENCE: 13

Trp Leu Ala Gly Leu Lys Glu
1               5

<210> SEQ ID NO 14
<211> LENGTH: 8
```

```
<212> TYPE: PRT
<213> ORGANISM: artificial sequence
<220> FEATURE:
<223> OTHER INFORMATION: synthetic peptide

<400> SEQUENCE: 14

Trp Leu Ala Gly Leu Lys Glu Gly
1               5

<210> SEQ ID NO 15
<211> LENGTH: 10
<212> TYPE: PRT
<213> ORGANISM: artificial sequence
<220> FEATURE:
<223> OTHER INFORMATION: synthetic peptide

<400> SEQUENCE: 15

Ala Gly Leu Thr Asn Gly Val Pro Gly Thr
1               5                   10

<210> SEQ ID NO 16
<211> LENGTH: 6
<212> TYPE: PRT
<213> ORGANISM: artificial sequence
<220> FEATURE:
<223> OTHER INFORMATION: synthetic peptide

<400> SEQUENCE: 16

Gly Thr Gly Leu Gly Asn
1               5

<210> SEQ ID NO 17
<211> LENGTH: 10
<212> TYPE: PRT
<213> ORGANISM: artificial sequence
<220> FEATURE:
<223> OTHER INFORMATION: synthetic peptide

<400> SEQUENCE: 17

Ser Pro Ala Asp Thr Gly Leu Gly Ala Arg
1               5                   10

<210> SEQ ID NO 18
<211> LENGTH: 8
<212> TYPE: PRT
<213> ORGANISM: artificial sequence
<220> FEATURE:
<223> OTHER INFORMATION: synthetic peptide

<400> SEQUENCE: 18

His Trp Thr Gly His Gly Ala Tyr
1               5

<210> SEQ ID NO 19
<211> LENGTH: 7
<212> TYPE: PRT
<213> ORGANISM: artificial sequence
<220> FEATURE:
<223> OTHER INFORMATION: synthetic peptide

<400> SEQUENCE: 19

Ala Gly Lys Gly Ala His Asn
1               5

<210> SEQ ID NO 20
<211> LENGTH: 8
<212> TYPE: PRT
```

```
<213> ORGANISM: artificial sequence
<220> FEATURE:
<223> OTHER INFORMATION: synthetic peptide

<400> SEQUENCE: 20

Ala Gly Lys Gly Ala His Asn Gly
1               5

<210> SEQ ID NO 21
<211> LENGTH: 8
<212> TYPE: PRT
<213> ORGANISM: artificial sequence
<220> FEATURE:
<223> OTHER INFORMATION: synthetic peptide

<400> SEQUENCE: 21

Trp Asp Gly Gly His Asn Ala Ile
1               5

<210> SEQ ID NO 22
<211> LENGTH: 7
<212> TYPE: PRT
<213> ORGANISM: artificial sequence
<220> FEATURE:
<223> OTHER INFORMATION: synthetic peptide

<400> SEQUENCE: 22

Trp Cys Leu Gly Gly Ser Ser
1               5

<210> SEQ ID NO 23
<211> LENGTH: 8
<212> TYPE: PRT
<213> ORGANISM: artificial sequence
<220> FEATURE:
<223> OTHER INFORMATION: synthetic peptide

<400> SEQUENCE: 23

Ala Ala Gly Trp Gly Gly Ser Asp
1               5

<210> SEQ ID NO 24
<211> LENGTH: 8
<212> TYPE: PRT
<213> ORGANISM: artificial sequence
<220> FEATURE:
<223> OTHER INFORMATION: synthetic peptide

<400> SEQUENCE: 24

Ala Arg Leu Ala Gly Trp Met Glu
1               5

<210> SEQ ID NO 25
<211> LENGTH: 7
<212> TYPE: PRT
<213> ORGANISM: artificial sequence
<220> FEATURE:
<223> OTHER INFORMATION: synthetic peptide

<400> SEQUENCE: 25

Gly Gly Ser Gly Val Met Glu
1               5

<210> SEQ ID NO 26
<211> LENGTH: 6
<212> TYPE: PRT
<213> ORGANISM: artificial sequence
```

```
<220> FEATURE:
<223> OTHER INFORMATION: synthetic peptide

<400> SEQUENCE: 26

Asp Thr Gly Gly Val Gly
1               5

<210> SEQ ID NO 27
<211> LENGTH: 8
<212> TYPE: PRT
<213> ORGANISM: artificial sequence
<220> FEATURE:
<223> OTHER INFORMATION: synthetic peptide

<400> SEQUENCE: 27

Gly Gly Val Asp Thr Gly Trp His
1               5

<210> SEQ ID NO 28
<211> LENGTH: 8
<212> TYPE: PRT
<213> ORGANISM: artificial sequence
<220> FEATURE:
<223> OTHER INFORMATION: synthetic peptide

<400> SEQUENCE: 28

Ala Ser Gly Val Asn Arg Gly Gly
1               5

<210> SEQ ID NO 29
<211> LENGTH: 8
<212> TYPE: PRT
<213> ORGANISM: artificial sequence
<220> FEATURE:
<223> OTHER INFORMATION: synthetic peptide

<400> SEQUENCE: 29

Glu Gly Val Trp Arg Ala Gly Asp
1               5

<210> SEQ ID NO 30
<211> LENGTH: 10
<212> TYPE: PRT
<213> ORGANISM: artificial sequence
<220> FEATURE:
<223> OTHER INFORMATION: synthetic peptide

<400> SEQUENCE: 30

Ser Ala Gly Gly Leu Asp Arg Gly Thr Ile
1               5                   10

<210> SEQ ID NO 31
<211> LENGTH: 7
<212> TYPE: PRT
<213> ORGANISM: artificial sequence
<220> FEATURE:
<223> OTHER INFORMATION: synthetic peptide

<400> SEQUENCE: 31

Gly Val Ser Asp Arg Gly Gln
1               5

<210> SEQ ID NO 32
<211> LENGTH: 10
<212> TYPE: PRT
<213> ORGANISM: artificial sequence
<220> FEATURE:
```

<223> OTHER INFORMATION: synthetic peptide

<400> SEQUENCE: 32

Ala Gly Pro Met Pro Val Thr Ala Ala Ser
1               5                   10

<210> SEQ ID NO 33
<211> LENGTH: 6
<212> TYPE: PRT
<213> ORGANISM: artificial sequence
<220> FEATURE:
<223> OTHER INFORMATION: synthetic peptide

<400> SEQUENCE: 33

Ser Tyr Pro Ala Gly Pro
1               5

<210> SEQ ID NO 34
<211> LENGTH: 10
<212> TYPE: PRT
<213> ORGANISM: artificial sequence
<220> FEATURE:
<223> OTHER INFORMATION: synthetic peptide

<400> SEQUENCE: 34

Gly Ser Ser Gly Pro Val Gln Val Thr Gly
1               5                   10

<210> SEQ ID NO 35
<211> LENGTH: 6
<212> TYPE: PRT
<213> ORGANISM: artificial sequence
<220> FEATURE:
<223> OTHER INFORMATION: synthetic peptide

<400> SEQUENCE: 35

Pro Ala Thr Val Val Gly
1               5

<210> SEQ ID NO 36
<211> LENGTH: 6
<212> TYPE: PRT
<213> ORGANISM: artificial sequence
<220> FEATURE:
<223> OTHER INFORMATION: synthetic peptide

<400> SEQUENCE: 36

Pro Arg Gly Asp Met Gly
1               5

<210> SEQ ID NO 37
<211> LENGTH: 10
<212> TYPE: PRT
<213> ORGANISM: artificial sequence
<220> FEATURE:
<223> OTHER INFORMATION: synthetic peptide

<400> SEQUENCE: 37

Gln Ile Cys Phe Met Pro Asp Gly Ser Ala
1               5                   10

<210> SEQ ID NO 38
<211> LENGTH: 10
<212> TYPE: PRT
<213> ORGANISM: artificial sequence
<220> FEATURE:
<223> OTHER INFORMATION: synthetic peptide

```
<400> SEQUENCE: 38

Cys Trp Ala Gly His Val Arg Gly Gln Gln
1               5                   10

<210> SEQ ID NO 39
<211> LENGTH: 6
<212> TYPE: PRT
<213> ORGANISM: artificial sequence
<220> FEATURE:
<223> OTHER INFORMATION: synthetic peptide

<400> SEQUENCE: 39

Arg Gly Ser Gln Ile Gln
1               5

<210> SEQ ID NO 40
<211> LENGTH: 6
<212> TYPE: PRT
<213> ORGANISM: artificial sequence
<220> FEATURE:
<223> OTHER INFORMATION: synthetic peptide

<400> SEQUENCE: 40

Val Arg Gly Leu Ile Pro
1               5

<210> SEQ ID NO 41
<211> LENGTH: 6
<212> TYPE: PRT
<213> ORGANISM: artificial sequence
<220> FEATURE:
<223> OTHER INFORMATION: synthetic peptide

<400> SEQUENCE: 41

Thr Thr Gln Glu Gly Lys
1               5

<210> SEQ ID NO 42
<211> LENGTH: 8
<212> TYPE: PRT
<213> ORGANISM: artificial sequence
<220> FEATURE:
<223> OTHER INFORMATION: synthetic peptide

<400> SEQUENCE: 42

Val Arg Gly Thr Gln Met Gly Ser
1               5

<210> SEQ ID NO 43
<211> LENGTH: 10
<212> TYPE: PRT
<213> ORGANISM: artificial sequence
<220> FEATURE:
<223> OTHER INFORMATION: synthetic peptide

<400> SEQUENCE: 43

Gln Arg Gly Gly Gly Ala Leu Val Pro Arg
1               5                   10

<210> SEQ ID NO 44
<211> LENGTH: 7
<212> TYPE: PRT
<213> ORGANISM: artificial sequence
<220> FEATURE:
<223> OTHER INFORMATION: synthetic peptide
```

```
<400> SEQUENCE: 44

Arg Gly Gly Arg Trp Glu Gly
1               5

<210> SEQ ID NO 45
<211> LENGTH: 8
<212> TYPE: PRT
<213> ORGANISM: artificial sequence
<220> FEATURE:
<223> OTHER INFORMATION: synthetic peptide

<400> SEQUENCE: 45

Ala Ala Arg Gly Glu Glu Ala Ala
1               5

<210> SEQ ID NO 46
<211> LENGTH: 7
<212> TYPE: PRT
<213> ORGANISM: artificial sequence
<220> FEATURE:
<223> OTHER INFORMATION: synthetic peptide

<400> SEQUENCE: 46

Cys Gly Thr Glu Gly Leu Val
1               5

<210> SEQ ID NO 47
<211> LENGTH: 10
<212> TYPE: PRT
<213> ORGANISM: artificial sequence
<220> FEATURE:
<223> OTHER INFORMATION: synthetic peptide

<400> SEQUENCE: 47

Thr Pro Gly Leu Gly Leu Gln Leu Ala Arg
1               5                   10

<210> SEQ ID NO 48
<211> LENGTH: 8
<212> TYPE: PRT
<213> ORGANISM: artificial sequence
<220> FEATURE:
<223> OTHER INFORMATION: synthetic peptide

<400> SEQUENCE: 48

Glu Ser Gly Cys Asp Gly Arg Lys
1               5

<210> SEQ ID NO 49
<211> LENGTH: 7
<212> TYPE: PRT
<213> ORGANISM: artificial sequence
<220> FEATURE:
<223> OTHER INFORMATION: synthetic peptide

<400> SEQUENCE: 49

Ser Gly Ser Thr Gly Arg Asn
1               5

<210> SEQ ID NO 50
<211> LENGTH: 6
<212> TYPE: PRT
<213> ORGANISM: artificial sequence
<220> FEATURE:
<223> OTHER INFORMATION: synthetic peptide

<400> SEQUENCE: 50
```

```
Glu Ala Lys Gly Arg Leu
1               5

<210> SEQ ID NO 51
<211> LENGTH: 8
<212> TYPE: PRT
<213> ORGANISM: artificial sequence
<220> FEATURE:
<223> OTHER INFORMATION: synthetic peptide

<400> SEQUENCE: 51

Gly Gly Tyr Gly Ala Ser Gly Arg
1               5

<210> SEQ ID NO 52
<211> LENGTH: 6
<212> TYPE: PRT
<213> ORGANISM: artificial sequence
<220> FEATURE:
<223> OTHER INFORMATION: synthetic peptide

<400> SEQUENCE: 52

Gly Arg Pro Gly Cys Asn
1               5

<210> SEQ ID NO 53
<211> LENGTH: 7
<212> TYPE: PRT
<213> ORGANISM: artificial sequence
<220> FEATURE:
<223> OTHER INFORMATION: synthetic peptide

<400> SEQUENCE: 53

Arg Arg Gly Arg Pro Gly Glu
1               5

<210> SEQ ID NO 54
<211> LENGTH: 8
<212> TYPE: PRT
<213> ORGANISM: artificial sequence
<220> FEATURE:
<223> OTHER INFORMATION: synthetic peptide

<400> SEQUENCE: 54

Gly Arg Ala Gly Met Lys Ser Thr
1               5

<210> SEQ ID NO 55
<211> LENGTH: 9
<212> TYPE: PRT
<213> ORGANISM: artificial sequence
<220> FEATURE:
<223> OTHER INFORMATION: synthetic peptide

<400> SEQUENCE: 55

Ser Gly Gly Met Ala Gly Arg Gly Met
1               5

<210> SEQ ID NO 56
<211> LENGTH: 10
<212> TYPE: PRT
<213> ORGANISM: artificial sequence
<220> FEATURE:
<223> OTHER INFORMATION: synthetic peptide

<400> SEQUENCE: 56
```

```
Ser Gly Gly Met Ala Gly Arg Gly Met Gly
1               5                   10

<210> SEQ ID NO 57
<211> LENGTH: 8
<212> TYPE: PRT
<213> ORGANISM: artificial sequence
<220> FEATURE:
<223> OTHER INFORMATION: synthetic peptide

<400> SEQUENCE: 57

Gly Gly Gln Ala Gly His Arg Arg
1               5

<210> SEQ ID NO 58
<211> LENGTH: 8
<212> TYPE: PRT
<213> ORGANISM: artificial sequence
<220> FEATURE:
<223> OTHER INFORMATION: synthetic peptide

<400> SEQUENCE: 58

Arg Ala Glu Gly Gly Gly Arg Gln
1               5

<210> SEQ ID NO 59
<211> LENGTH: 10
<212> TYPE: PRT
<213> ORGANISM: artificial sequence
<220> FEATURE:
<223> OTHER INFORMATION: synthetic peptide

<400> SEQUENCE: 59

Ser Arg Cys Lys Gly Gly Gln Gly Gln Thr
1               5                   10

<210> SEQ ID NO 60
<211> LENGTH: 8
<212> TYPE: PRT
<213> ORGANISM: artificial sequence
<220> FEATURE:
<223> OTHER INFORMATION: synthetic peptide

<400> SEQUENCE: 60

Arg Phe Asp Gly Arg Gly Arg Ser
1               5

<210> SEQ ID NO 61
<211> LENGTH: 8
<212> TYPE: PRT
<213> ORGANISM: artificial sequence
<220> FEATURE:
<223> OTHER INFORMATION: synthetic peptide

<400> SEQUENCE: 61

Ile Pro Gly Gly Arg Tyr Gln Arg
1               5

<210> SEQ ID NO 62
<211> LENGTH: 6
<212> TYPE: PRT
<213> ORGANISM: artificial sequence
<220> FEATURE:
<223> OTHER INFORMATION: synthetic peptide

<400> SEQUENCE: 62

Gly Pro Gly Arg Arg Cys
```

<210> SEQ ID NO 63
<211> LENGTH: 6
<212> TYPE: PRT
<213> ORGANISM: artificial sequence
<220> FEATURE:
<223> OTHER INFORMATION: synthetic peptide

<400> SEQUENCE: 63

Gly Arg Ala Val Cys Ala
1               5

<210> SEQ ID NO 64
<211> LENGTH: 6
<212> TYPE: PRT
<213> ORGANISM: artificial sequence
<220> FEATURE:
<223> OTHER INFORMATION: synthetic peptide

<400> SEQUENCE: 64

Gly Arg Thr Val Ser Ala
1               5

<210> SEQ ID NO 65
<211> LENGTH: 10
<212> TYPE: PRT
<213> ORGANISM: artificial sequence
<220> FEATURE:
<223> OTHER INFORMATION: synthetic peptide

<400> SEQUENCE: 65

Gly Arg Ser Val Glu His His Arg Ser Asp
1               5                   10

<210> SEQ ID NO 66
<211> LENGTH: 8
<212> TYPE: PRT
<213> ORGANISM: artificial sequence
<220> FEATURE:
<223> OTHER INFORMATION: synthetic peptide

<400> SEQUENCE: 66

Asn Arg Thr Thr Gly Arg Ser Ser
1               5

<210> SEQ ID NO 67
<211> LENGTH: 6
<212> TYPE: PRT
<213> ORGANISM: artificial sequence
<220> FEATURE:
<223> OTHER INFORMATION: synthetic peptide

<400> SEQUENCE: 67

Ala Asn Gly Arg Glu Arg
1               5

<210> SEQ ID NO 68
<211> LENGTH: 8
<212> TYPE: PRT
<213> ORGANISM: artificial sequence
<220> FEATURE:
<223> OTHER INFORMATION: synthetic peptide

<400> SEQUENCE: 68

Ala Asn Gly Arg Glu Arg Gly Asp
1               5

<210> SEQ ID NO 69
<211> LENGTH: 8
<212> TYPE: PRT
<213> ORGANISM: artificial sequence
<220> FEATURE:
<223> OTHER INFORMATION: synthetic peptide

<400> SEQUENCE: 69

Met Leu Asn Asn Arg Cys Arg Asp
1               5

<210> SEQ ID NO 70
<211> LENGTH: 10
<212> TYPE: PRT
<213> ORGANISM: artificial sequence
<220> FEATURE:
<223> OTHER INFORMATION: synthetic peptide

<400> SEQUENCE: 70

Gly Thr Ala Asp Ala Cys Arg Gln His Cys
1               5                   10

<210> SEQ ID NO 71
<211> LENGTH: 8
<212> TYPE: PRT
<213> ORGANISM: artificial sequence
<220> FEATURE:
<223> OTHER INFORMATION: synthetic peptide

<400> SEQUENCE: 71

Leu Ala Asn Ala Gly Arg Ser His
1               5

<210> SEQ ID NO 72
<211> LENGTH: 8
<212> TYPE: PRT
<213> ORGANISM: artificial sequence
<220> FEATURE:
<223> OTHER INFORMATION: synthetic peptide

<400> SEQUENCE: 72

Val Gly Ala Ser Arg Arg Arg Arg
1               5

<210> SEQ ID NO 73
<211> LENGTH: 8
<212> TYPE: PRT
<213> ORGANISM: artificial sequence
<220> FEATURE:
<223> OTHER INFORMATION: synthetic peptide

<400> SEQUENCE: 73

Val Gly Trp Ser Arg Arg Arg Arg
1               5

<210> SEQ ID NO 74
<211> LENGTH: 10
<212> TYPE: PRT
<213> ORGANISM: artificial sequence
<220> FEATURE:
<223> OTHER INFORMATION: synthetic peptide

<400> SEQUENCE: 74

Pro Gly Glu Thr Val Gly Ser Ser Arg Ser
1               5                   10

```
<210> SEQ ID NO 75
<211> LENGTH: 8
<212> TYPE: PRT
<213> ORGANISM: artificial sequence
<220> FEATURE:
<223> OTHER INFORMATION: synthetic peptide

<400> SEQUENCE: 75

Gly Thr Val His Gln Arg Arg Ser
1               5

<210> SEQ ID NO 76
<211> LENGTH: 6
<212> TYPE: PRT
<213> ORGANISM: artificial sequence
<220> FEATURE:
<223> OTHER INFORMATION: synthetic peptide

<400> SEQUENCE: 76

Tyr Val Gly Glu Tyr Ile
1               5

<210> SEQ ID NO 77
<211> LENGTH: 8
<212> TYPE: PRT
<213> ORGANISM: artificial sequence
<220> FEATURE:
<223> OTHER INFORMATION: synthetic peptide

<400> SEQUENCE: 77

Phe Tyr His Gly Asp Ser His Ser
1               5

<210> SEQ ID NO 78
<211> LENGTH: 8
<212> TYPE: PRT
<213> ORGANISM: artificial sequence
<220> FEATURE:
<223> OTHER INFORMATION: synthetic peptide

<400> SEQUENCE: 78

Arg Val Arg Cys Gly Ser Ser Ala
1               5

<210> SEQ ID NO 79
<211> LENGTH: 7
<212> TYPE: PRT
<213> ORGANISM: artificial sequence
<220> FEATURE:
<223> OTHER INFORMATION: synthetic peptide

<400> SEQUENCE: 79

Pro Leu Arg Val Gly Ser Ser
1               5

<210> SEQ ID NO 80
<211> LENGTH: 8
<212> TYPE: PRT
<213> ORGANISM: artificial sequence
<220> FEATURE:
<223> OTHER INFORMATION: synthetic peptide

<400> SEQUENCE: 80

Arg Ser Arg Arg Gly Ser Glu Thr
1               5
```

<210> SEQ ID NO 81
<211> LENGTH: 10
<212> TYPE: PRT
<213> ORGANISM: artificial sequence
<220> FEATURE:
<223> OTHER INFORMATION: synthetic peptide

<400> SEQUENCE: 81

Gly Gln Ser Arg Thr Pro Ser Asp Thr Cys
1               5                   10

<210> SEQ ID NO 82
<211> LENGTH: 6
<212> TYPE: PRT
<213> ORGANISM: artificial sequence
<220> FEATURE:
<223> OTHER INFORMATION: synthetic peptide

<400> SEQUENCE: 82

Trp Ala Pro Phe Gln His
1               5

<210> SEQ ID NO 83
<211> LENGTH: 6
<212> TYPE: PRT
<213> ORGANISM: artificial sequence
<220> FEATURE:
<223> OTHER INFORMATION: synthetic peptide

<400> SEQUENCE: 83

Trp Lys Ser Gly Gln His
1               5

<210> SEQ ID NO 84
<211> LENGTH: 8
<212> TYPE: PRT
<213> ORGANISM: artificial sequence
<220> FEATURE:
<223> OTHER INFORMATION: synthetic peptide

<400> SEQUENCE: 84

Leu Lys Thr Arg Gln Val Trp Lys
1               5

<210> SEQ ID NO 85
<211> LENGTH: 10
<212> TYPE: PRT
<213> ORGANISM: artificial sequence
<220> FEATURE:
<223> OTHER INFORMATION: synthetic peptide

<400> SEQUENCE: 85

Leu Lys Thr Arg Gln Val Trp Lys Gly Asp
1               5                   10

<210> SEQ ID NO 86
<211> LENGTH: 8
<212> TYPE: PRT
<213> ORGANISM: artificial sequence
<220> FEATURE:
<223> OTHER INFORMATION: synthetic peptide

<400> SEQUENCE: 86

Arg Ile Val Trp Ala Trp Lys Glu
1               5

<210> SEQ ID NO 87

```
<211> LENGTH: 10
<212> TYPE: PRT
<213> ORGANISM: artificial sequence
<220> FEATURE:
<223> OTHER INFORMATION: synthetic peptide

<400> SEQUENCE: 87

Cys Val Lys Asp Tyr Glu Ser Ala Ser Phe
1               5                   10

<210> SEQ ID NO 88
<211> LENGTH: 8
<212> TYPE: PRT
<213> ORGANISM: artificial sequence
<220> FEATURE:
<223> OTHER INFORMATION: synthetic peptide

<400> SEQUENCE: 88

Lys Ser Tyr Gly Arg Ala Arg Tyr
1               5

<210> SEQ ID NO 89
<211> LENGTH: 8
<212> TYPE: PRT
<213> ORGANISM: artificial sequence
<220> FEATURE:
<223> OTHER INFORMATION: synthetic peptide

<400> SEQUENCE: 89

Lys Ser Cys Gln Lys Glu Arg His
1               5

<210> SEQ ID NO 90
<211> LENGTH: 6
<212> TYPE: PRT
<213> ORGANISM: artificial sequence
<220> FEATURE:
<223> OTHER INFORMATION: synthetic peptide

<400> SEQUENCE: 90

Arg Ser Ala Gln Gly His
1               5

<210> SEQ ID NO 91
<211> LENGTH: 8
<212> TYPE: PRT
<213> ORGANISM: artificial sequence
<220> FEATURE:
<223> OTHER INFORMATION: synthetic peptide

<400> SEQUENCE: 91

His Met Lys Ala Gln Tyr His Ser
1               5

<210> SEQ ID NO 92
<211> LENGTH: 10
<212> TYPE: PRT
<213> ORGANISM: artificial sequence
<220> FEATURE:
<223> OTHER INFORMATION: synthetic peptide

<400> SEQUENCE: 92

Asn Phe Arg Tyr Cys Ser Leu Ala Arg Ser
1               5                   10

<210> SEQ ID NO 93
<211> LENGTH: 8
```

```
<212> TYPE: PRT
<213> ORGANISM: artificial sequence
<220> FEATURE:
<223> OTHER INFORMATION: synthetic peptide

<400> SEQUENCE: 93

Gly Ala Pro Trp Ala Arg Ser Gly
1               5

<210> SEQ ID NO 94
<211> LENGTH: 10
<212> TYPE: PRT
<213> ORGANISM: artificial sequence
<220> FEATURE:
<223> OTHER INFORMATION: synthetic peptide

<400> SEQUENCE: 94

His Met Arg Ser Ser Ser Met Val Leu Leu
1               5                   10

<210> SEQ ID NO 95
<211> LENGTH: 7
<212> TYPE: PRT
<213> ORGANISM: artificial sequence
<220> FEATURE:
<223> OTHER INFORMATION: synthetic peptide

<400> SEQUENCE: 95

Arg Ala Arg Arg Met Val Ala
1               5

<210> SEQ ID NO 96
<211> LENGTH: 7
<212> TYPE: PRT
<213> ORGANISM: artificial sequence
<220> FEATURE:
<223> OTHER INFORMATION: synthetic peptide

<400> SEQUENCE: 96

Ala Arg Pro Ser Val Leu His
1               5

<210> SEQ ID NO 97
<211> LENGTH: 10
<212> TYPE: PRT
<213> ORGANISM: artificial sequence
<220> FEATURE:
<223> OTHER INFORMATION: synthetic peptide

<400> SEQUENCE: 97

His Ser Glu Glu Tyr Pro Ser Met Leu Leu
1               5                   10

<210> SEQ ID NO 98
<211> LENGTH: 10
<212> TYPE: PRT
<213> ORGANISM: artificial sequence
<220> FEATURE:
<223> OTHER INFORMATION: synthetic peptide

<400> SEQUENCE: 98

Cys Val Val Tyr Phe Arg Leu Asn Ser Asn
1               5                   10

<210> SEQ ID NO 99
<211> LENGTH: 8
<212> TYPE: PRT
```

```
<213> ORGANISM: artificial sequence
<220> FEATURE:
<223> OTHER INFORMATION: synthetic peptide

<400> SEQUENCE: 99

Tyr Tyr Gly Thr Leu Ser Asn Ser
1               5

<210> SEQ ID NO 100
<211> LENGTH: 8
<212> TYPE: PRT
<213> ORGANISM: artificial sequence
<220> FEATURE:
<223> OTHER INFORMATION: synthetic peptide

<400> SEQUENCE: 100

Gly Ala Val His Ala Ser Glu Arg
1               5

<210> SEQ ID NO 101
<211> LENGTH: 10
<212> TYPE: PRT
<213> ORGANISM: artificial sequence
<220> FEATURE:
<223> OTHER INFORMATION: synthetic peptide

<400> SEQUENCE: 101

Thr Ala Lys Arg Ala Ser Asp Arg Asn Thr
1               5                   10

<210> SEQ ID NO 102
<211> LENGTH: 6
<212> TYPE: PRT
<213> ORGANISM: artificial sequence
<220> FEATURE:
<223> OTHER INFORMATION: synthetic peptide

<400> SEQUENCE: 102

Lys Lys Arg Ser Phe Asp
1               5

<210> SEQ ID NO 103
<211> LENGTH: 7
<212> TYPE: PRT
<213> ORGANISM: artificial sequence
<220> FEATURE:
<223> OTHER INFORMATION: synthetic peptide

<400> SEQUENCE: 103

His Lys Lys Glu Ser Arg Ser
1               5

<210> SEQ ID NO 104
<211> LENGTH: 8
<212> TYPE: PRT
<213> ORGANISM: artificial sequence
<220> FEATURE:
<223> OTHER INFORMATION: synthetic peptide

<400> SEQUENCE: 104

Thr Arg Ser Glu Asp Ser Val Thr
1               5

<210> SEQ ID NO 105
<211> LENGTH: 10
<212> TYPE: PRT
<213> ORGANISM: artificial sequence
```

```
<220> FEATURE:
<223> OTHER INFORMATION: synthetic peptide

<400> SEQUENCE: 105

Ala Pro Asp Lys Asn Ser Arg Val Thr Gln
1               5                   10

<210> SEQ ID NO 106
<211> LENGTH: 6
<212> TYPE: PRT
<213> ORGANISM: artificial sequence
<220> FEATURE:
<223> OTHER INFORMATION: synthetic peptide

<400> SEQUENCE: 106

Gly Val Pro Lys Ser His
1               5

<210> SEQ ID NO 107
<211> LENGTH: 10
<212> TYPE: PRT
<213> ORGANISM: artificial sequence
<220> FEATURE:
<223> OTHER INFORMATION: synthetic peptide

<400> SEQUENCE: 107

Cys Met Thr Gly Asn Asp Lys Ser Asp Arg
1               5                   10

<210> SEQ ID NO 108
<211> LENGTH: 10
<212> TYPE: PRT
<213> ORGANISM: artificial sequence
<220> FEATURE:
<223> OTHER INFORMATION: synthetic peptide

<400> SEQUENCE: 108

Gly Asn Asp Lys Asp Arg Val Asp Arg Arg
1               5                   10

<210> SEQ ID NO 109
<211> LENGTH: 7
<212> TYPE: PRT
<213> ORGANISM: artificial sequence
<220> FEATURE:
<223> OTHER INFORMATION: synthetic peptide

<400> SEQUENCE: 109

Ile Ser Thr Phe Gly Thr Thr
1               5

<210> SEQ ID NO 110
<211> LENGTH: 10
<212> TYPE: PRT
<213> ORGANISM: artificial sequence
<220> FEATURE:
<223> OTHER INFORMATION: synthetic peptide

<400> SEQUENCE: 110

Ile Ser Thr Phe Gly Thr Thr Gly Glu Leu
1               5                   10

<210> SEQ ID NO 111
<211> LENGTH: 8
<212> TYPE: PRT
<213> ORGANISM: artificial sequence
<220> FEATURE:
```

<223> OTHER INFORMATION: synthetic peptide

<400> SEQUENCE: 111

Phe Thr Phe Thr Thr Thr Gly Tyr
1               5

<210> SEQ ID NO 112
<211> LENGTH: 6
<212> TYPE: PRT
<213> ORGANISM: artificial sequence
<220> FEATURE:
<223> OTHER INFORMATION: synthetic peptide

<400> SEQUENCE: 112

Phe Asp Lys Thr Lys Trp
1               5

<210> SEQ ID NO 113
<211> LENGTH: 6
<212> TYPE: PRT
<213> ORGANISM: artificial sequence
<220> FEATURE:
<223> OTHER INFORMATION: synthetic peptide

<400> SEQUENCE: 113

Ser Phe Gln Leu Arg Lys
1               5

<210> SEQ ID NO 114
<211> LENGTH: 8
<212> TYPE: PRT
<213> ORGANISM: artificial sequence
<220> FEATURE:
<223> OTHER INFORMATION: synthetic peptide

<400> SEQUENCE: 114

Ser Val Arg Gln Lys Arg Lys Val
1               5

<210> SEQ ID NO 115
<211> LENGTH: 9
<212> TYPE: PRT
<213> ORGANISM: artificial sequence
<220> FEATURE:
<223> OTHER INFORMATION: synthetic peptide

<400> SEQUENCE: 115

Val Ala Ala Asp Arg Lys Val Gly Thr
1               5

<210> SEQ ID NO 116
<211> LENGTH: 10
<212> TYPE: PRT
<213> ORGANISM: artificial sequence
<220> FEATURE:
<223> OTHER INFORMATION: synthetic peptide

<400> SEQUENCE: 116

Val Ala Ala Asp Arg Lys Val Gly Thr Gly
1               5                   10

<210> SEQ ID NO 117
<211> LENGTH: 6
<212> TYPE: PRT
<213> ORGANISM: artificial sequence
<220> FEATURE:
<223> OTHER INFORMATION: synthetic peptide

```
<400> SEQUENCE: 117

Val Cys Leu Arg Arg Phe
1               5

<210> SEQ ID NO 118
<211> LENGTH: 7
<212> TYPE: PRT
<213> ORGANISM: artificial sequence
<220> FEATURE:
<223> OTHER INFORMATION: synthetic peptide

<400> SEQUENCE: 118

Arg Glu Val Cys Val Pro Arg
1               5

<210> SEQ ID NO 119
<211> LENGTH: 7
<212> TYPE: PRT
<213> ORGANISM: artificial sequence
<220> FEATURE:
<223> OTHER INFORMATION: synthetic peptide

<400> SEQUENCE: 119

Leu Thr Gln Val Asn Tyr Val
1               5

<210> SEQ ID NO 120
<211> LENGTH: 6
<212> TYPE: PRT
<213> ORGANISM: artificial sequence
<220> FEATURE:
<223> OTHER INFORMATION: synthetic peptide

<400> SEQUENCE: 120

Lys Cys Leu Arg Gln Pro
1               5

<210> SEQ ID NO 121
<211> LENGTH: 6
<212> TYPE: PRT
<213> ORGANISM: artificial sequence
<220> FEATURE:
<223> OTHER INFORMATION: synthetic peptide

<400> SEQUENCE: 121

Gln Ala Leu Ser Asn Phe
1               5

<210> SEQ ID NO 122
<211> LENGTH: 10
<212> TYPE: PRT
<213> ORGANISM: artificial sequence
<220> FEATURE:
<223> OTHER INFORMATION: synthetic peptide

<400> SEQUENCE: 122

Ala Leu Asp Asn Thr Thr Tyr Glu Gln Ser
1               5                   10

<210> SEQ ID NO 123
<211> LENGTH: 7
<212> TYPE: PRT
<213> ORGANISM: artificial sequence
<220> FEATURE:
<223> OTHER INFORMATION: synthetic peptide
```

```
<400> SEQUENCE: 123

Leu Val Asn Ile Thr Arg Leu
1               5

<210> SEQ ID NO 124
<211> LENGTH: 10
<212> TYPE: PRT
<213> ORGANISM: artificial sequence
<220> FEATURE:
<223> OTHER INFORMATION: synthetic peptide

<400> SEQUENCE: 124

Leu Cys Arg Leu Lys Pro Arg Leu Arg Asn
1               5                   10

<210> SEQ ID NO 125
<211> LENGTH: 6
<212> TYPE: PRT
<213> ORGANISM: artificial sequence
<220> FEATURE:
<223> OTHER INFORMATION: synthetic peptide

<400> SEQUENCE: 125

Leu Lys Pro Leu Thr Pro
1               5

<210> SEQ ID NO 126
<211> LENGTH: 10
<212> TYPE: PRT
<213> ORGANISM: artificial sequence
<220> FEATURE:
<223> OTHER INFORMATION: synthetic peptide

<400> SEQUENCE: 126

Ile Lys Ser Pro Leu Ala Ser Arg Pro Phe
1               5                   10

<210> SEQ ID NO 127
<211> LENGTH: 7
<212> TYPE: PRT
<213> ORGANISM: artificial sequence
<220> FEATURE:
<223> OTHER INFORMATION: synthetic peptide

<400> SEQUENCE: 127

Lys Cys Ser Pro Leu Ile Asn
1               5

<210> SEQ ID NO 128
<211> LENGTH: 8
<212> TYPE: PRT
<213> ORGANISM: artificial sequence
<220> FEATURE:
<223> OTHER INFORMATION: synthetic peptide

<400> SEQUENCE: 128

Gly Ala Asn Ala Ser Pro Leu Arg
1               5

<210> SEQ ID NO 129
<211> LENGTH: 8
<212> TYPE: PRT
<213> ORGANISM: artificial sequence
<220> FEATURE:
<223> OTHER INFORMATION: synthetic peptide

<400> SEQUENCE: 129
```

Val Ala Val Arg Pro Ser Ala Ala
1               5

<210> SEQ ID NO 130
<211> LENGTH: 10
<212> TYPE: PRT
<213> ORGANISM: artificial sequence
<220> FEATURE:
<223> OTHER INFORMATION: synthetic peptide

<400> SEQUENCE: 130

Gly Leu Gly Val Glu Val Gln Pro Asp Ala
1               5                   10

<210> SEQ ID NO 131
<211> LENGTH: 8
<212> TYPE: PRT
<213> ORGANISM: artificial sequence
<220> FEATURE:
<223> OTHER INFORMATION: synthetic peptide

<400> SEQUENCE: 131

Leu Val Ala Val Ile Phe Ser Thr
1               5

<210> SEQ ID NO 132
<211> LENGTH: 8
<212> TYPE: PRT
<213> ORGANISM: artificial sequence
<220> FEATURE:
<223> OTHER INFORMATION: synthetic peptide

<400> SEQUENCE: 132

Gln Val Val Pro Val Met Arg Thr
1               5

<210> SEQ ID NO 133
<211> LENGTH: 7
<212> TYPE: PRT
<213> ORGANISM: artificial sequence
<220> FEATURE:
<223> OTHER INFORMATION: synthetic peptide

<400> SEQUENCE: 133

Phe Val Ile Pro Val Arg Cys
1               5

<210> SEQ ID NO 134
<211> LENGTH: 7
<212> TYPE: PRT
<213> ORGANISM: artificial sequence
<220> FEATURE:
<223> OTHER INFORMATION: synthetic peptide

<400> SEQUENCE: 134

Pro Thr Val His Cys Ser Ala
1               5

<210> SEQ ID NO 135
<211> LENGTH: 8
<212> TYPE: PRT
<213> ORGANISM: artificial sequence
<220> FEATURE:
<223> OTHER INFORMATION: synthetic peptide

<400> SEQUENCE: 135

Ala Leu Pro Thr Tyr His Leu Ser
1               5

<210> SEQ ID NO 136
<211> LENGTH: 10
<212> TYPE: PRT
<213> ORGANISM: artificial sequence
<220> FEATURE:
<223> OTHER INFORMATION: synthetic peptide

<400> SEQUENCE: 136

Val Lys Ala Gly Ala Cys Ser Ala Ile Ser
1               5                   10

<210> SEQ ID NO 137
<211> LENGTH: 8
<212> TYPE: PRT
<213> ORGANISM: artificial sequence
<220> FEATURE:
<223> OTHER INFORMATION: synthetic peptide

<400> SEQUENCE: 137

Cys Asn Arg Ala Cys Pro Ala Ile
1               5

<210> SEQ ID NO 138
<211> LENGTH: 6
<212> TYPE: PRT
<213> ORGANISM: artificial sequence
<220> FEATURE:
<223> OTHER INFORMATION: synthetic peptide

<400> SEQUENCE: 138

Gly Ala Tyr Thr Ser Lys
1               5

<210> SEQ ID NO 139
<211> LENGTH: 8
<212> TYPE: PRT
<213> ORGANISM: artificial sequence
<220> FEATURE:
<223> OTHER INFORMATION: synthetic peptide

<400> SEQUENCE: 139

Asn Met Pro Gln Ala Tyr Ala Ser
1               5

<210> SEQ ID NO 140
<211> LENGTH: 8
<212> TYPE: PRT
<213> ORGANISM: artificial sequence
<220> FEATURE:
<223> OTHER INFORMATION: synthetic peptide

<400> SEQUENCE: 140

Pro Gly Ala Val Thr Gly Tyr Ala
1               5

<210> SEQ ID NO 141
<211> LENGTH: 7
<212> TYPE: PRT
<213> ORGANISM: artificial sequence
<220> FEATURE:
<223> OTHER INFORMATION: synthetic peptide

<400> SEQUENCE: 141

Gly Ala Trp Thr Arg Val Ala

```
<210> SEQ ID NO 142
<211> LENGTH: 8
<212> TYPE: PRT
<213> ORGANISM: artificial sequence
<220> FEATURE:
<223> OTHER INFORMATION: synthetic peptide

<400> SEQUENCE: 142

Pro Gly Thr Met Ala Pro Ala Ala
1               5

<210> SEQ ID NO 143
<211> LENGTH: 8
<212> TYPE: PRT
<213> ORGANISM: artificial sequence
<220> FEATURE:
<223> OTHER INFORMATION: synthetic peptide

<400> SEQUENCE: 143

Glu Gly Ala Lys Ala Met Ala Ala
1               5

<210> SEQ ID NO 144
<211> LENGTH: 6
<212> TYPE: PRT
<213> ORGANISM: artificial sequence
<220> FEATURE:
<223> OTHER INFORMATION: synthetic peptide

<400> SEQUENCE: 144

Gln Pro Ala Met Gly Ala
1               5

<210> SEQ ID NO 145
<211> LENGTH: 7
<212> TYPE: PRT
<213> ORGANISM: artificial sequence
<220> FEATURE:
<223> OTHER INFORMATION: synthetic peptide

<400> SEQUENCE: 145

Leu Val Pro Ser Arg Trp Thr
1               5

<210> SEQ ID NO 146
<211> LENGTH: 8
<212> TYPE: PRT
<213> ORGANISM: artificial sequence
<220> FEATURE:
<223> OTHER INFORMATION: synthetic peptide

<400> SEQUENCE: 146

Leu Val Pro Ser Arg Trp Thr Gly
1               5

<210> SEQ ID NO 147
<211> LENGTH: 10
<212> TYPE: PRT
<213> ORGANISM: artificial sequence
<220> FEATURE:
<223> OTHER INFORMATION: synthetic peptide

<400> SEQUENCE: 147

Asn Val Pro Ala Ala Trp Asn Gln Tyr Asn
1               5                   10
```

<210> SEQ ID NO 148
<211> LENGTH: 8
<212> TYPE: PRT
<213> ORGANISM: artificial sequence
<220> FEATURE:
<223> OTHER INFORMATION: synthetic peptide

<400> SEQUENCE: 148

Cys Glu Ser Val Pro Gly Ala Gly
1               5

<210> SEQ ID NO 149
<211> LENGTH: 6
<212> TYPE: PRT
<213> ORGANISM: artificial sequence
<220> FEATURE:
<223> OTHER INFORMATION: synthetic peptide

<400> SEQUENCE: 149

Cys Glu Ser Val Pro Gly
1               5

<210> SEQ ID NO 150
<211> LENGTH: 10
<212> TYPE: PRT
<213> ORGANISM: artificial sequence
<220> FEATURE:
<223> OTHER INFORMATION: synthetic peptide

<400> SEQUENCE: 150

Val Gln Glu Ala Cys Glu Ser Asp Pro His
1               5                   10

<210> SEQ ID NO 151
<211> LENGTH: 8
<212> TYPE: PRT
<213> ORGANISM: artificial sequence
<220> FEATURE:
<223> OTHER INFORMATION: synthetic peptide

<400> SEQUENCE: 151

Arg Thr Val Arg Glu Cys Glu Gln
1               5

<210> SEQ ID NO 152
<211> LENGTH: 8
<212> TYPE: PRT
<213> ORGANISM: artificial sequence
<220> FEATURE:
<223> OTHER INFORMATION: synthetic peptide

<400> SEQUENCE: 152

Val Arg Ala Gly Glu Ala Arg Arg
1               5

<210> SEQ ID NO 153
<211> LENGTH: 6
<212> TYPE: PRT
<213> ORGANISM: artificial sequence
<220> FEATURE:
<223> OTHER INFORMATION: synthetic peptide

<400> SEQUENCE: 153

Arg Ala Glu Met Pro Tyr
1               5

<210> SEQ ID NO 154
<211> LENGTH: 10
<212> TYPE: PRT
<213> ORGANISM: artificial sequence
<220> FEATURE:
<223> OTHER INFORMATION: synthetic peptide

<400> SEQUENCE: 154

Arg Ala Glu His Val Arg Val Ala Glu Arg
1               5                   10

<210> SEQ ID NO 155
<211> LENGTH: 7
<212> TYPE: PRT
<213> ORGANISM: artificial sequence
<220> FEATURE:
<223> OTHER INFORMATION: synthetic peptide

<400> SEQUENCE: 155

Arg Ala Cys Gly Pro Cys Lys
1               5

<210> SEQ ID NO 156
<211> LENGTH: 10
<212> TYPE: PRT
<213> ORGANISM: artificial sequence
<220> FEATURE:
<223> OTHER INFORMATION: synthetic peptide

<400> SEQUENCE: 156

Gly Phe His Ser Pro Met Ser Gln Arg Asn
1               5                   10

<210> SEQ ID NO 157
<211> LENGTH: 8
<212> TYPE: PRT
<213> ORGANISM: artificial sequence
<220> FEATURE:
<223> OTHER INFORMATION: synthetic peptide

<400> SEQUENCE: 157

Ser Ala His Gln Pro Arg Cys Gln
1               5

<210> SEQ ID NO 158
<211> LENGTH: 8
<212> TYPE: PRT
<213> ORGANISM: artificial sequence
<220> FEATURE:
<223> OTHER INFORMATION: synthetic peptide

<400> SEQUENCE: 158

Arg His Asp Val Ser Cys Gly Phe
1               5

<210> SEQ ID NO 159
<211> LENGTH: 10
<212> TYPE: PRT
<213> ORGANISM: artificial sequence
<220> FEATURE:
<223> OTHER INFORMATION: synthetic peptide

<400> SEQUENCE: 159

Val Arg His Asp Val Asp Gln Met Ile
1               5                   10

```
<210> SEQ ID NO 160
<211> LENGTH: 10
<212> TYPE: PRT
<213> ORGANISM: artificial sequence
<220> FEATURE:
<223> OTHER INFORMATION: synthetic peptide

<400> SEQUENCE: 160

Lys Gln Gly Arg His Leu Gln Ala Gly Thr
1               5                   10

<210> SEQ ID NO 161
<211> LENGTH: 7
<212> TYPE: PRT
<213> ORGANISM: artificial sequence
<220> FEATURE:
<223> OTHER INFORMATION: synthetic peptide

<400> SEQUENCE: 161

His Gln Gly Pro Arg Leu Ile
1               5

<210> SEQ ID NO 162
<211> LENGTH: 8
<212> TYPE: PRT
<213> ORGANISM: artificial sequence
<220> FEATURE:
<223> OTHER INFORMATION: synthetic peptide

<400> SEQUENCE: 162

Gly Val Cys Ser Asp Lys Trp Lys
1               5

<210> SEQ ID NO 163
<211> LENGTH: 6
<212> TYPE: PRT
<213> ORGANISM: artificial sequence
<220> FEATURE:
<223> OTHER INFORMATION: synthetic peptide

<400> SEQUENCE: 163

Gln Gly Val Leu Val Asp
1               5

<210> SEQ ID NO 164
<211> LENGTH: 8
<212> TYPE: PRT
<213> ORGANISM: artificial sequence
<220> FEATURE:
<223> OTHER INFORMATION: synthetic peptide

<400> SEQUENCE: 164

Asn Gln Gln Gly Met Arg Ser Asp
1               5

<210> SEQ ID NO 165
<211> LENGTH: 6
<212> TYPE: PRT
<213> ORGANISM: artificial sequence
<220> FEATURE:
<223> OTHER INFORMATION: synthetic peptide

<400> SEQUENCE: 165

Cys Gly Thr Ala Val Ala
1               5

<210> SEQ ID NO 166
```

```
<211> LENGTH: 6
<212> TYPE: PRT
<213> ORGANISM: artificial sequence
<220> FEATURE:
<223> OTHER INFORMATION: synthetic peptide

<400> SEQUENCE: 166

Cys Asn Thr Ser Val Ser
1               5

<210> SEQ ID NO 167
<211> LENGTH: 10
<212> TYPE: PRT
<213> ORGANISM: artificial sequence
<220> FEATURE:
<223> OTHER INFORMATION: synthetic peptide

<400> SEQUENCE: 167

Trp Asn Thr His Thr Leu Leu Trp Gly Thr
1               5                   10

<210> SEQ ID NO 168
<211> LENGTH: 5
<212> TYPE: PRT
<213> ORGANISM: artificial sequence
<220> FEATURE:
<223> OTHER INFORMATION: synthetic peptide

<400> SEQUENCE: 168

Thr Arg Ala Leu Pro
1               5

<210> SEQ ID NO 169
<211> LENGTH: 7
<212> TYPE: PRT
<213> ORGANISM: artificial sequence
<220> FEATURE:
<223> OTHER INFORMATION: synthetic peptide

<400> SEQUENCE: 169

Thr Arg Ala Leu Pro Gly Ala
1               5

<210> SEQ ID NO 170
<211> LENGTH: 10
<212> TYPE: PRT
<213> ORGANISM: artificial sequence
<220> FEATURE:
<223> OTHER INFORMATION: synthetic peptide

<400> SEQUENCE: 170

Arg Pro Leu Val Cys Arg Ala Leu Pro Ser
1               5                   10

<210> SEQ ID NO 171
<211> LENGTH: 8
<212> TYPE: PRT
<213> ORGANISM: artificial sequence
<220> FEATURE:
<223> OTHER INFORMATION: synthetic peptide

<400> SEQUENCE: 171

Ser Arg Asp Leu Pro Arg Asp Ser
1               5

<210> SEQ ID NO 172
<211> LENGTH: 6
```

<212> TYPE: PRT
<213> ORGANISM: artificial sequence
<220> FEATURE:
<223> OTHER INFORMATION: synthetic peptide

<400> SEQUENCE: 172

Asp Cys Arg Thr Leu Ala
1               5

<210> SEQ ID NO 173
<211> LENGTH: 10
<212> TYPE: PRT
<213> ORGANISM: artificial sequence
<220> FEATURE:
<223> OTHER INFORMATION: synthetic peptide

<400> SEQUENCE: 173

Glu Thr Glu Phe Phe Met Ser Arg Lys Leu
1               5                   10

<210> SEQ ID NO 174
<211> LENGTH: 6
<212> TYPE: PRT
<213> ORGANISM: artificial sequence
<220> FEATURE:
<223> OTHER INFORMATION: synthetic peptide

<400> SEQUENCE: 174

Glu Thr Leu Thr Phe Lys
1               5

<210> SEQ ID NO 175
<211> LENGTH: 7
<212> TYPE: PRT
<213> ORGANISM: artificial sequence
<220> FEATURE:
<223> OTHER INFORMATION: synthetic peptide

<400> SEQUENCE: 175

Val Glu Pro Asn Pro Phe Leu
1               5

<210> SEQ ID NO 176
<211> LENGTH: 8
<212> TYPE: PRT
<213> ORGANISM: artificial sequence
<220> FEATURE:
<223> OTHER INFORMATION: synthetic peptide

<400> SEQUENCE: 176

Asn Asp Phe Leu Ala Ser Thr Thr
1               5

<210> SEQ ID NO 177
<211> LENGTH: 7
<212> TYPE: PRT
<213> ORGANISM: artificial sequence
<220> FEATURE:
<223> OTHER INFORMATION: synthetic peptide

<400> SEQUENCE: 177

Ser Thr Ser Thr Thr Phe Pro
1               5

<210> SEQ ID NO 178
<211> LENGTH: 10
<212> TYPE: PRT

```
<213> ORGANISM: artificial sequence
<220> FEATURE:
<223> OTHER INFORMATION: synthetic peptide

<400> SEQUENCE: 178

Trp His Ser Ser Glu Phe Arg Gly Lys Tyr
1               5                   10

<210> SEQ ID NO 179
<211> LENGTH: 7
<212> TYPE: PRT
<213> ORGANISM: artificial sequence
<220> FEATURE:
<223> OTHER INFORMATION: synthetic peptide

<400> SEQUENCE: 179

His Thr Glu Val Phe Arg Asp
1               5

<210> SEQ ID NO 180
<211> LENGTH: 9
<212> TYPE: PRT
<213> ORGANISM: artificial sequence
<220> FEATURE:
<223> OTHER INFORMATION: synthetic peptide

<400> SEQUENCE: 180

Leu Val Leu Tyr Leu Ala Phe Arg Arg
1               5

<210> SEQ ID NO 181
<211> LENGTH: 8
<212> TYPE: PRT
<213> ORGANISM: artificial sequence
<220> FEATURE:
<223> OTHER INFORMATION: synthetic peptide

<400> SEQUENCE: 181

Ala Phe Arg Phe Glu Asn Asp Pro
1               5

<210> SEQ ID NO 182
<211> LENGTH: 6
<212> TYPE: PRT
<213> ORGANISM: artificial sequence
<220> FEATURE:
<223> OTHER INFORMATION: synthetic peptide

<400> SEQUENCE: 182

Val Leu Gly Ser Asn Ser
1               5

<210> SEQ ID NO 183
<211> LENGTH: 10
<212> TYPE: PRT
<213> ORGANISM: artificial sequence
<220> FEATURE:
<223> OTHER INFORMATION: synthetic peptide

<400> SEQUENCE: 183

Ser Gln Asp Ile Arg Ala Val Leu Gly Ser
1               5                   10

<210> SEQ ID NO 184
<211> LENGTH: 7
<212> TYPE: PRT
<213> ORGANISM: artificial sequence
```

<220> FEATURE:
<223> OTHER INFORMATION: synthetic peptide

<400> SEQUENCE: 184

Val Leu Gly Lys Thr Cys Asp
1               5

<210> SEQ ID NO 185
<211> LENGTH: 8
<212> TYPE: PRT
<213> ORGANISM: artificial sequence
<220> FEATURE:
<223> OTHER INFORMATION: synthetic peptide

<400> SEQUENCE: 185

Met His Ala Arg Leu Arg Val Glu
1               5

<210> SEQ ID NO 186
<211> LENGTH: 6
<212> TYPE: PRT
<213> ORGANISM: artificial sequence
<220> FEATURE:
<223> OTHER INFORMATION: synthetic peptide

<400> SEQUENCE: 186

Ala Cys Ala Val Leu Arg
1               5

<210> SEQ ID NO 187
<211> LENGTH: 8
<212> TYPE: PRT
<213> ORGANISM: artificial sequence
<220> FEATURE:
<223> OTHER INFORMATION: synthetic peptide

<400> SEQUENCE: 187

Thr Ala Ile Lys Lys Met Lys Ser
1               5

<210> SEQ ID NO 188
<211> LENGTH: 10
<212> TYPE: PRT
<213> ORGANISM: artificial sequence
<220> FEATURE:
<223> OTHER INFORMATION: synthetic peptide

<400> SEQUENCE: 188

Val Ala Ile Lys Arg Pro Gly Lys Gly Thr
1               5                   10

<210> SEQ ID NO 189
<211> LENGTH: 10
<212> TYPE: PRT
<213> ORGANISM: artificial sequence
<220> FEATURE:
<223> OTHER INFORMATION: synthetic peptide

<400> SEQUENCE: 189

Leu Ala Ser Leu Gly Ala Gly Lys Cys Lys
1               5                   10

<210> SEQ ID NO 190
<211> LENGTH: 8
<212> TYPE: PRT
<213> ORGANISM: artificial sequence
<220> FEATURE:

```
<223> OTHER INFORMATION: synthetic peptide

<400> SEQUENCE: 190

Val Ala Ile Leu Gly Ala Asp Tyr
1               5

<210> SEQ ID NO 191
<211> LENGTH: 6
<212> TYPE: PRT
<213> ORGANISM: artificial sequence
<220> FEATURE:
<223> OTHER INFORMATION: synthetic peptide

<400> SEQUENCE: 191

Trp Arg Thr Glu Ile Ile
1               5

<210> SEQ ID NO 192
<211> LENGTH: 8
<212> TYPE: PRT
<213> ORGANISM: artificial sequence
<220> FEATURE:
<223> OTHER INFORMATION: synthetic peptide

<400> SEQUENCE: 192

Gly Glu Gly Trp Arg Asp Glu Arg
1               5

<210> SEQ ID NO 193
<211> LENGTH: 7
<212> TYPE: PRT
<213> ORGANISM: artificial sequence
<220> FEATURE:
<223> OTHER INFORMATION: synthetic peptide

<400> SEQUENCE: 193

Lys Gly Ala Gly Trp Arg Trp
1               5

<210> SEQ ID NO 194
<211> LENGTH: 8
<212> TYPE: PRT
<213> ORGANISM: artificial sequence
<220> FEATURE:
<223> OTHER INFORMATION: synthetic peptide

<400> SEQUENCE: 194

Lys Gly Ala Gly Trp Arg Trp Gly
1               5

<210> SEQ ID NO 195
<211> LENGTH: 7
<212> TYPE: PRT
<213> ORGANISM: artificial sequence
<220> FEATURE:
<223> OTHER INFORMATION: synthetic peptide

<400> SEQUENCE: 195

Glu Tyr Arg Gln Ser Arg Arg
1               5

<210> SEQ ID NO 196
<211> LENGTH: 8
<212> TYPE: PRT
<213> ORGANISM: artificial sequence
<220> FEATURE:
<223> OTHER INFORMATION: synthetic peptide
```

<400> SEQUENCE: 196

Ile Asn Met Arg Gln Ser Lys Ser
1               5

<210> SEQ ID NO 197
<211> LENGTH: 6
<212> TYPE: PRT
<213> ORGANISM: artificial sequence
<220> FEATURE:
<223> OTHER INFORMATION: synthetic peptide

<400> SEQUENCE: 197

Leu Glu Met Arg Lys Asn
1               5

<210> SEQ ID NO 198
<211> LENGTH: 10
<212> TYPE: PRT
<213> ORGANISM: artificial sequence
<220> FEATURE:
<223> OTHER INFORMATION: synthetic peptide

<400> SEQUENCE: 198

Arg Lys Ser Ala Ser Gln Lys Gly Met Cys
1               5                   10

<210> SEQ ID NO 199
<211> LENGTH: 10
<212> TYPE: PRT
<213> ORGANISM: artificial sequence
<220> FEATURE:
<223> OTHER INFORMATION: synthetic peptide

<400> SEQUENCE: 199

Met Val Glu Gln Ser Gly Glu Val Ser Asn
1               5                   10

<210> SEQ ID NO 200
<211> LENGTH: 6
<212> TYPE: PRT
<213> ORGANISM: artificial sequence
<220> FEATURE:
<223> OTHER INFORMATION: synthetic peptide

<400> SEQUENCE: 200

Arg Asn Ser Gly Tyr Phe
1               5

<210> SEQ ID NO 201
<211> LENGTH: 8
<212> TYPE: PRT
<213> ORGANISM: artificial sequence
<220> FEATURE:
<223> OTHER INFORMATION: synthetic peptide

<400> SEQUENCE: 201

Ser Thr His Asp His Glu Val Leu
1               5

<210> SEQ ID NO 202
<211> LENGTH: 10
<212> TYPE: PRT
<213> ORGANISM: artificial sequence
<220> FEATURE:
<223> OTHER INFORMATION: synthetic peptide

```
<400> SEQUENCE: 202

Arg Pro Glu Gln Ser Arg Asp Gly Ala Thr
1               5                   10

<210> SEQ ID NO 203
<211> LENGTH: 7
<212> TYPE: PRT
<213> ORGANISM: artificial sequence
<220> FEATURE:
<223> OTHER INFORMATION: synthetic peptide

<400> SEQUENCE: 203

Cys Gln Leu Thr Ala Phe Pro
1               5

<210> SEQ ID NO 204
<211> LENGTH: 10
<212> TYPE: PRT
<213> ORGANISM: artificial sequence
<220> FEATURE:
<223> OTHER INFORMATION: synthetic peptide

<400> SEQUENCE: 204

Trp Gln Gln Val Pro Phe Cys Ser His His
1               5                   10

<210> SEQ ID NO 205
<211> LENGTH: 8
<212> TYPE: PRT
<213> ORGANISM: artificial sequence
<220> FEATURE:
<223> OTHER INFORMATION: synthetic peptide

<400> SEQUENCE: 205

Val Arg Ala Ala Arg Glu Gly Arg
1               5

<210> SEQ ID NO 206
<211> LENGTH: 8
<212> TYPE: PRT
<213> ORGANISM: artificial sequence
<220> FEATURE:
<223> OTHER INFORMATION: synthetic peptide

<400> SEQUENCE: 206

Ser Ala Ile Lys Lys Pro Val Ala
1               5

<210> SEQ ID NO 207
<211> LENGTH: 8
<212> TYPE: PRT
<213> ORGANISM: artificial sequence
<220> FEATURE:
<223> OTHER INFORMATION: synthetic peptide

<400> SEQUENCE: 207

Thr Ala Ile Lys Lys Lys Lys Ser
1               5

<210> SEQ ID NO 208
<211> LENGTH: 8
<212> TYPE: PRT
<213> ORGANISM: artificial sequence
<220> FEATURE:
<223> OTHER INFORMATION: synthetic peptide

<400> SEQUENCE: 208
```

Thr Ala Ile Lys Lys Met Glu Ser
1               5

<210> SEQ ID NO 209
<211> LENGTH: 8
<212> TYPE: PRT
<213> ORGANISM: artificial sequence
<220> FEATURE:
<223> OTHER INFORMATION: synthetic peptide

<400> SEQUENCE: 209

Thr Ala Ile Lys Lys Met Lys Pro
1               5

<210> SEQ ID NO 210
<211> LENGTH: 8
<212> TYPE: PRT
<213> ORGANISM: artificial sequence
<220> FEATURE:
<223> OTHER INFORMATION: synthetic peptide

<400> SEQUENCE: 210

Thr Ala Ile Lys Lys Met Lys Tyr
1               5

<210> SEQ ID NO 211
<211> LENGTH: 7
<212> TYPE: PRT
<213> ORGANISM: artificial sequence
<220> FEATURE:
<223> OTHER INFORMATION: synthetic peptide

<400> SEQUENCE: 211

Thr Ala Ile Lys Lys Arg Thr
1               5

<210> SEQ ID NO 212
<211> LENGTH: 8
<212> TYPE: PRT
<213> ORGANISM: artificial sequence
<220> FEATURE:
<223> OTHER INFORMATION: synthetic peptide

<400> SEQUENCE: 212

Tyr Ala Ile Lys Lys Pro Val Thr
1               5

<210> SEQ ID NO 213
<211> LENGTH: 10
<212> TYPE: PRT
<213> ORGANISM: artificial sequence
<220> FEATURE:
<223> OTHER INFORMATION: synthetic peptide

<400> SEQUENCE: 213

Val Ala Ile Lys Arg Pro Gly Arg Gly Thr
1               5                   10

<210> SEQ ID NO 214
<211> LENGTH: 10
<212> TYPE: PRT
<213> ORGANISM: artificial sequence
<220> FEATURE:
<223> OTHER INFORMATION: synthetic peptide

<400> SEQUENCE: 214

Val Ala Ile Lys Arg Pro Phe Glu Phe Thr
1               5                   10

<210> SEQ ID NO 215
<211> LENGTH: 6
<212> TYPE: PRT
<213> ORGANISM: artificial sequence
<220> FEATURE:
<223> OTHER INFORMATION: synthetic peptide

<400> SEQUENCE: 215

Val Ala Ile Lys Arg Pro
1               5

<210> SEQ ID NO 216
<211> LENGTH: 10
<212> TYPE: PRT
<213> ORGANISM: artificial sequence
<220> FEATURE:
<223> OTHER INFORMATION: synthetic peptide

<400> SEQUENCE: 216

Val Ala Ile Lys Pro Ala Arg Gln Gly Thr
1               5                   10

<210> SEQ ID NO 217
<211> LENGTH: 7
<212> TYPE: PRT
<213> ORGANISM: artificial sequence
<220> FEATURE:
<223> OTHER INFORMATION: synthetic peptide

<400> SEQUENCE: 217

Thr Ala Ile Lys Lys Arg Thr
1               5

<210> SEQ ID NO 218
<211> LENGTH: 8
<212> TYPE: PRT
<213> ORGANISM: artificial sequence
<220> FEATURE:
<223> OTHER INFORMATION: synthetic peptide

<400> SEQUENCE: 218

Thr Ala Ile Lys Lys Met Lys Tyr
1               5

<210> SEQ ID NO 219
<211> LENGTH: 8
<212> TYPE: PRT
<213> ORGANISM: artificial sequence
<220> FEATURE:
<223> OTHER INFORMATION: synthetic peptide

<400> SEQUENCE: 219

Thr Ala Ile Lys Lys Met Lys Pro
1               5

<210> SEQ ID NO 220
<211> LENGTH: 8
<212> TYPE: PRT
<213> ORGANISM: artificial sequence
<220> FEATURE:
<223> OTHER INFORMATION: synthetic peptide

<400> SEQUENCE: 220

Thr Ala Ile Lys Lys Met Glu Ser

```
1               5

<210> SEQ ID NO 221
<211> LENGTH: 7
<212> TYPE: PRT
<213> ORGANISM: artificial sequence
<220> FEATURE:
<223> OTHER INFORMATION: synthetic peptide

<400> SEQUENCE: 221

Thr Ala Ile Lys Lys Lys Ser
1               5

<210> SEQ ID NO 222
<211> LENGTH: 8
<212> TYPE: PRT
<213> ORGANISM: artificial sequence
<220> FEATURE:
<223> OTHER INFORMATION: synthetic peptide

<400> SEQUENCE: 222

Ser Ala Ile Lys Lys Pro Val Ala
1               5

<210> SEQ ID NO 223
<211> LENGTH: 10
<212> TYPE: PRT
<213> ORGANISM: artificial sequence
<220> FEATURE:
<223> OTHER INFORMATION: synthetic peptide

<400> SEQUENCE: 223

Gly Ala Ile Lys Arg Pro Gly Lys Gly Thr
1               5                   10

<210> SEQ ID NO 224
<211> LENGTH: 10
<212> TYPE: PRT
<213> ORGANISM: artificial sequence
<220> FEATURE:
<223> OTHER INFORMATION: synthetic peptide

<400> SEQUENCE: 224

Ala Ala Ile Lys Arg Pro Gly Lys Gly Thr
1               5                   10

<210> SEQ ID NO 225
<211> LENGTH: 8
<212> TYPE: PRT
<213> ORGANISM: artificial sequence
<220> FEATURE:
<223> OTHER INFORMATION: synthetic peptide

<400> SEQUENCE: 225

Tyr Ala Ile Lys Lys Pro Val Thr
1               5

<210> SEQ ID NO 226
<211> LENGTH: 4
<212> TYPE: PRT
<213> ORGANISM: artificial sequence
<220> FEATURE:
<223> OTHER INFORMATION: synthetic peptide
<220> FEATURE:
<221> NAME/KEY: misc_feature
<222> LOCATION: (4)..(4)
<223> OTHER INFORMATION: Xaa can be either Lys or Arg
```

```
<400> SEQUENCE: 226

Ala Ile Lys Xaa
1

<210> SEQ ID NO 227
<211> LENGTH: 4
<212> TYPE: PRT
<213> ORGANISM: artificial sequence
<220> FEATURE:
<223> OTHER INFORMATION: synthetic peptide

<400> SEQUENCE: 227

Ala Ile Lys Lys
1

<210> SEQ ID NO 228
<211> LENGTH: 4
<212> TYPE: PRT
<213> ORGANISM: artificial sequence
<220> FEATURE:
<223> OTHER INFORMATION: synthetic peptide

<400> SEQUENCE: 228

Ala Ile Lys Arg
1

<210> SEQ ID NO 229
<211> LENGTH: 10
<212> TYPE: PRT
<213> ORGANISM: artificial sequence
<220> FEATURE:
<223> OTHER INFORMATION: synthetic peptide

<400> SEQUENCE: 229

Gly Asp Tyr Thr Asp Tyr Lys Ser Asp Asp
1               5                   10

<210> SEQ ID NO 230
<211> LENGTH: 10
<212> TYPE: PRT
<213> ORGANISM: artificial sequence
<220> FEATURE:
<223> OTHER INFORMATION: synthetic peptide

<400> SEQUENCE: 230

Asp Thr Phe Met Asp Tyr Lys Ser Arg Asp
1               5                   10

<210> SEQ ID NO 231
<211> LENGTH: 12
<212> TYPE: PRT
<213> ORGANISM: artificial sequence
<220> FEATURE:
<223> OTHER INFORMATION: synthetic peptide

<400> SEQUENCE: 231

His Leu Leu Ser Glu Gly Asp Tyr Lys Ser Ser Asp
1               5                   10

<210> SEQ ID NO 232
<211> LENGTH: 10
<212> TYPE: PRT
<213> ORGANISM: artificial sequence
<220> FEATURE:
<223> OTHER INFORMATION: synthetic peptide

<400> SEQUENCE: 232
```

```
Asp Thr Arg Asp Tyr Lys Leu Ala Asp Phe
1               5                   10

<210> SEQ ID NO 233
<211> LENGTH: 10
<212> TYPE: PRT
<213> ORGANISM: artificial sequence
<220> FEATURE:
<223> OTHER INFORMATION: synthetic peptide

<400> SEQUENCE: 233

Leu Asp Tyr Asn Asp Tyr Lys Ser Arg Asp
1               5                   10
```